(12) United States Patent
Gan et al.

(10) Patent No.: US 6,340,584 B1
(45) Date of Patent: Jan. 22, 2002

(54) ISOLATED HUMAN KINASE PROTEINS, NUCLEIC ACID MOLECULES ENCODING HUMAN KINASE PROTEINS, AND USES THEREOF

(75) Inventors: Weiniu Gan, Gaithersburg; Jane Ye, Boyds; Valentina Di Francesco, Rockville; Ellen M. Beasley, Darnestown, all of MD (US)

(73) Assignee: PE Corporation (NY), Norwalk, CT (US)

( * ) Notice: Subject to any disclaimer, the term of this patent is extended or adjusted under 35 U.S.C. 154(b) by 0 days.

(21) Appl. No.: 09/817,180

(22) Filed: Mar. 27, 2001

(51) Int. Cl.[7] .............................. C12N 9/12; C12N 1/20; C12N 15/00; C12N 5/00; C07H 21/04
(52) U.S. Cl. .................... 435/194; 435/320.1; 435/325; 435/252.3; 536/23.2
(58) Field of Search ............................... 435/194, 320.1, 435/252.3, 325; 536/23.2

(56) References Cited

PUBLICATIONS

Van de Ven et al., EP 0246709 and itscorresponding sequence alignment with SEQ ID No.:3, Nov. 1987.*

* cited by examiner

*Primary Examiner*—Rebecca E. Prouty
(74) *Attorney, Agent, or Firm*—Celera Genomics; Robert A. Millman; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

9 Claims, 19 Drawing Sheets

```
   1 TCCGGGGTCC GCACCGGGCC TGAGTCGGTC CGAGGCCGTC CCAGGAGCAG
  51 CTGCCCGTGC GGAACAGCAC TATGGGCTTC TCTTCTGAGC TGTGCAGCCC
 101 CCAGGGCCAC GGGGTCCTGC AGCAAATGCA GGAGGCCGAG CTTCGTCTAC
 151 TGGAGGGCAT GAGAAAGTGG ATGGCCCAGC GGGTCAAGAG TGACAGGGAG
 201 TATGCAGGAC TGCTTCACCA CATGTCCCTG CAGGACAGTG GGGGCCAGAG
 251 CCGGGCCATC AGCCCTGACA GCCCCATCAG TCAGTCCTGG GCTGAGATCA
 301 CCAGCCAAAC TGAGGGCCTG AGCCGCTTGC TGCGGCAGCA CGCAGAGGAT
 351 CTGAACTCAG GGCCCCTGAG CAAGCTGAGC CTGCTCATCC GGGAACGGCA
 401 GCAGCTTCGC AAGACCTACA GCGAGCAGTG GCAGCAGCTG CAGCAGGAGC
 451 TCACCAAGAC CCACAGCCAG GACATTGAGA AGCTGAAGAG CCAGTACCGA
 501 GCTCTGGCAC GGGACAGTGC CCAAGCCAAG CGCAAGTACC AGGAGGCCAG
 551 CAAAGACAAG GACCGTGACA AGGCCAAGGA CAAGTATGTG CGCAGCCTGT
 601 GGAAGCTCTT TGCTCACCAC AACCGCTATG TGCTGGGCGT GCGGGCTGCG
 651 CAGCTACACC ACCAGCACCA CCACCAGCTC CTGCTGCCCG GCCTGCTGCG
 701 GTCACTGCAG GACCTGCACG AGGAGATGGC TTGCATCCTG AAGGAGATCC
 751 TGCAGGAATA CCTGGAGATT AGCAGCCTGG TGCAGGATGA GGTGGTGGCC
 801 ATTCACCGGG AGATGGCTGC AGCTGCTGCC CGCATCCAGC TGAGGCTGA
 851 GTACCAAGGC TTCCTGCGAC AGTATGGGTC CGCACCTGAC GTCCCACCCT
 901 GTGTCACGTT CGATGAGTCA CTGCTTGAGG AGGGTGAACC GCTGGAGCCT
 951 GGGGAGCTCC AGCTGAACGA GCTGACTGTG GAGAGCGTGC AGCACACGCT
1001 GACCTCAGTG ACAGATGAGC TGGCTGTGGC CACCGAGATG GTGTTCAGGC
1051 GGCAGGAGAT GGTTACGCAG CTGCAACAGG AGCTCCGGAA TGAAGAGGAG
1101 AACACCCACC CCCGGGAGCG GGTGCAGCTG CTGGGCAAGA GGCAAGTGCT
1151 GCAAGAAGCA CTGCAGGGGC TGCAGGTAGC GCTGTGCAGC CAGGCCAAGC
1201 TGCAGGCCCA GCAGGAGTTG CTGCAGACCA AGCTGGAGCA CCTGGGCCCC
1251 GGCGAGCCCC CGCCTGTGCT GCTCCTGCAG GATGACCGCC ACTCCACGTC
1301 GTCCTCGGAG CAGGAGCGAG AGGGGGGAAG GACACCCACG CTGGAGATCC
1351 TTAAGAGCCA CATCTCAGGA ATCTTCCGCC CCAAGTTCTC GAACCTGTAC
1401 CGACTGGAAG GGGAAGGCTT TCCTAGCATT CCTTTGCTCA TCGACCACCT
1451 ACTGAGCACC CAGCAGCCCC TCACCAAGAA GAGTGGTGTT GTCCTGCACA
1501 GGGCTGTGCC CAAGGACAAG TGGGTGCTGA ACCATGAGGA CCTGGTGTTG
1551 GGTGAGCAGA TTGGACGGGG GAACTTTGGC GAAGTGTTCA GCGGACGCCT
1601 GCGAGCCGAC AACACCCTGG TGGCGGTGAA GTCTTGTCGA GAGACGCTCC
1651 CACCTGACCT CAAGGCCAAG TTTCTACAGG AAGCGAGGAT CCTGAAGCAG
1701 TACAGCCACC CCAACATCGT GCGTCTCATT GGTGTCTGCA CCCAGAAGCA
1751 GCCCATCTAC ATCGTCATGG AGCTTGTGCA GGGGGGCGAC TTCCTGACCT
1801 TCCTCCGCAC GGAGGGGGCC CGCCTGCGGG TGAAGACTCT GCTGCAGATG
1851 GTGGGGGATG CAGCTGCTGG CATGGAGTAC CTGGAGAGCA AGTGCTGCAT
1901 CCACCGGGAC CTGGCTGCTC GGAACTGCCT GGTGACAGAG AAGAATGTCC
1951 TGAAGATCAG TGACTTTGGG ATGTCCCGAG AGGAAGCCGA TGGGGTCTAT
2001 GCAGCCTCAG GGGGCCTCAG ACAAGTCCCC GTGAAGTGGA CCGCACCTGA
2051 GGCCCTTAAC TACGGCCGCT ACTCCTCCGA AAGCGACGTG TGGAGCTTTG
2101 GCATCTTGCT CTGGGAGACC TTCAGCCTGG GGGCCTCCCC CTATCCCAAC
2151 CTCAGCAATC AGCAGACACG GGAGTTTGTG GAGAAGGGGG CCGTCTGCC
2201 CTGCCCAGAG CTGTGTCCTG ATGCCGTGTT CAGGCTCATG GAGCAGTGCT
2251 GGGCCTATGA GCCTGGGCAG CGGCCCAGCT TCAGCACCAT CTACCAGGAG
```

FIG. 1A

```
2301 CTGCAGAGCA TCCGAAAGCG GCATCGGTGA GGCTGGGACC CCCTTCTCAA
2351 GCTGGTGGCC TCTGCAGGCC TAGGTGCAGC TCCTCAGCGG CTCCAGCTCA
2401 TATGCTGACA GCTCTTCACA GTCCTGGACT CCTGCCACCA GCATCCACAC
2451 TGCCGGCAGG ATGCAGCGCC GTGTCCTCTC TGTGTCCCTG CTGCTGCCAG
2501 GGCTTCCTCT TCCGGGCAGA AACAATAAAA CCACTTGTGC CCACTGAAAA
2551 AAAAAAAAAA AAAAAAAAAA AAAAAAAAAA AAAAAAAAAA AAAAAAAAAA
2601 AAAAAAAAAA AAAAAAAAAA AAAAAAAAAA AAAAAAAAAA AAAAAAAAAA
2651 AAAAAAAAAA AAAAAAAAAA AAAA   (SEQ ID NO:1)
```

FEATURES:
5'UTR:        1-71
Start Codon:  72
Stop Codon:   2328
3'UTR:        2331

Homologous proteins:
Top 10 BLAST Hits

|  | Score | E |
|---|---|---|
| CRA\|18000004928524 /altid=gi\|4503687 /def=ref\|NP_001996.1\| feli... | 1364 | 0.0 |
| CRA\|18000004928925 /altid=gi\|400127 /def=sp\|P07332\|FES_HUMAN PR... | 1361 | 0.0 |
| CRA\|335001098689057 /altid=gi\|11433086 /def=ref\|XP_007718.1\| fe... | 1361 | 0.0 |
| CRA\|18000004944482 /altid=gi\|66835 /def=pir\|\|TVCTFF protein-tyr... | 1285 | 0.0 |
| CRA\|18000004883448 /altid=gi\|1345986 /def=sp\|P14238\|FES_FELCA P... | 1285 | 0.0 |
| CRA\|18000004938794 /altid=gi\|125356 /def=sp\|P16879\|FES_MOUSE PR... | 1249 | 0.0 |
| CRA\|18000004944484 /altid=gi\|125354 /def=sp\|P00543\|FES_FSVST TY... | 647 | 0.0 |
| CRA\|18000004958077 /altid=gi\|323873 /def=gb\|AAA43041.1\| (J02087... | 621 | e-176 |
| CRA\|18000004944483 /altid=gi\|125353 /def=sp\|P00542\|FES_FSVGA TY... | 621 | e-176 |
| CRA\|108000000500738 /altid=gi\|7548235 /def=gb\|AAA43046.2\| (J020... | 603 | e-171 |

BLAST dbEST hits:

|  | Score | E |
|---|---|---|
| gi\|12875454 /dataset=dbest /taxon=960... | 1669 | 0.0 |
| gi\|12259598 /dataset=dbest /taxon=960... | 924 | 0.0 |
| gi\|5526793 /dataset=dbest /taxon=9606 ... | 856 | 0.0 |
| gi\|1501859 /dataset=dbest /taxon=9606 ... | 722 | 0.0 |
| gi\|9097978 /dataset=dbest /taxon=9606... | 714 | 0.0 |
| gi\|6131861 /dataset=dbest /taxon=9606 ... | 682 | 0.0 |
| gi\|12447497 /dataset=dbest /taxon=96... | 674 | 0.0 |

FIG. 1B

EXPRESSION INFORMATION FOR MODULATORY USE:
library source:
From BLAST dbEST hits:
gi|12875454  Placenta
gi|12259598  Lung-tumor
gi|5526793   Kidney 2 pooled tumors
gi|1501859   Pregnant uterus
gi|9097978   Pediatric ore-B cell lymphoblastic leukemia
gi|6131861   Stomach poorly differentiated adenocarcinoma with signet ring ells
gi|12447497  Placenta normal From tissue screening panels:
Hippocampus

FIG. 1C

```
  1 MGFSSELCSP QGHGVLQQMQ EAELRLLEGM RKWMAQRVKS DREYAGLLHH
 51 MSLQDSGGQS RAISPDSPIS QSWAEITSQT EGLSRLLRQH AEDLNSGPLS
101 KLSLLIRERQ QLRKTYSEQW QQLQQELTKT HSQDIEKLKS QYRALARDSA
151 QAKRKYQEAS KDKDRDKAKD KYVRSLWKLF AHHNRYVLGV RAAQLHHQHH
201 HQLLLPGLLR SLQDLHEEMA CILKEILQEY LEISSLVQDE VVAIHREMAA
251 AAARIQPEAE YQGFLRQYGS APDVPPCVTF DESLLEEGEP LEPGELQLNE
301 LTVESVQHTL TSVTDELAVA TEMVFRRQEM VTQLQQELRN EEENTHPRER
351 VQLLGKRQVL QEALQGLQVA LCSQAKLQAQ QELLQTKLEH LGPGEPPPVL
401 LLQDDRHSTS SSEQEREGGR TPTLEILKSH ISGIFRPKFS NLYRLEGEGF
451 PSIPLLIDHL LSTQQPLTKK SGVVLHRAVP KDKWVLNHED LVLGEQIGRG
501 NFGEVFSGRL RADNTLVAVK SCRETLPPDL KAKFLQEARI LKQYSHPNIV
551 RLIGVCTQKQ PIYIVMELVQ GGDFLTFLRT EGARLRVKTL LQMVGDAAAG
601 MEYLESKCCI HRDLAARNCL VTEKNVLKIS DFGMSREEAD GVYAASGGLR
651 QVPVKWTAPE ALNYGRYSSE SDVWSFGILL WETFSLGASP YPNLSNQQTR
701 EFVEKGGRLP CPELCPDAVF RLMEQCWAYE PGQRPSFSTI YQELQSIRKR
751 HR  (SEQ ID NO:2)
```

FEATURES:
Functional domains and key regions:
[1] PDOC00001 PS00001 ASN_GLYCOSYLATION
N-glycosylation site 693-696 NLSN

[2] PDOC00005 PS00005 PKC_PHOSPHO_SITE
Protein kinase C phosphorylation site

Number of matches: 7
    1     40-42 SDR
    2   468-470 TKK
    3   507-509 SGR
    4   521-523 SCR
    5   557-559 TQK
    6   622-624 TEK
    7   746-748 SIR

[3] PDOC00006 PS00006 CK2_PHOSPHO_SITE
Casein kinase II phosphorylation site

FIG. 2A

Number of matches: 17
```
     1      40-43  SDRE
     2      52-55  SLQD
     3     211-214 SLQD
     4      72-75  SWAE
     5      78-81  SQTE
     6     115-118 TYSE
     7      52-55  SLQD
     8     211-214 SLQD
     9     270-273 SAPD
    10     279-282 TFDE
    11     283-286 SLLE
    12     312-315 SVTD
    13     386-389 TKLE
    14     410-413 SSSE
    15     412-415 SEQE
    16     521-524 SCRE
    17     635-638 SREE
```

[4] PDOC00007 PS00007 TYR_PHOSPHO_SITE
Tyrosine kinase phosphorylation site

Number of matches: 3
```
    1    37-44  RVKSDREY
    2   254-261 RIQPEAEY
    3   636-643 REEADGVY
```

[5] PDOC00008 PS00008 MYRISTYL
N-myristoylation site

Number of matches: 6
```
    1    58-63  GQSRAI
    2   189-194 GVRAAQ
    3   207-212 GLLRSL
    4   366-371 GLQVAL
    5   641-646 GVYAAS
    6   732-737 GQRPSF
```

[6] PDOC00009 PS00009 AMIDATION
Amidation site

```
        354-357 LGKR
```

FIG. 2B

[7] PDOC00100 PS00107 PROTEIN_KINASE_ATP
Protein kinases ATP-binding region signature 497-520 IGRGNFGEVFSGRLRADNTLVAVK

[8] PDOC00100 PS00109 PROTEIN_KINASE_TYR
Tyrosine protein kinases specific active-site signature 609-621 CIHRDLAARNCLV Membrane spanning structure and domains:
```
 Helix Begin   End   Score Certainty
   1    672    692   1.129 Certain
```

BLAST Alignment to Top Hit:
```
>CRA|18000004928524 /altid=gi|4503687 /def=ref|NP_001996.1| feline
        sarcoma (Snyder-Theilen) viral (v-fes)/Fujinami avian
        sarcoma (PRCII) viral (v-fps) oncogene homolog; Oncogene
        FES, feline sarcoma virus [Homo sapiens] /org=Homo
        sapiens /taxon=9606 /dataset=nraa /length=822
     Length = 822
```

Score = 1364 bits (3491), Expect = 0.0
Identities = 706/822 (85%), Positives = 716/822 (86%), Gaps = 70/822 (8%)
Frame = +3

```
Query: 72   MGFSSELCSPQGHGVLQQMQEAELRLLEGMRKWMAQRVKSDREYAGLLHHMSLQDSGGQS 251
            MGFSSELCSPQGHGVLQQMQEAELRLLEGMRKWMAQRVKSDREYAGLLHHMSLQDSGGQS
Sbjct: 1    MGFSSELCSPQGHGVLQQMQEAELRLLEGMRKWMAQRVKSDREYAGLLHHMSLQDSGGQS 60

Query: 252  RAISPDSPISQSWAEITSQTEGLSRLLRQHAEDLNSGPLSKLSLLIRERQQLRKTYSEQW 431
            RAISPDSPISQSWAEITSQTEGLSRLLRQHAEDLNSGPLSKLSLLIRERQQLRKTYSEQW
Sbjct: 61   RAISPDSPISQSWAEITSQTEGLSRLLRQHAEDLNSGPLSKLSLLIRERQQLRKTYSEQW 120

Query: 432  QQLQQELTKTHSQDIEKLKSQYRALARDSAQAKRKYQEASKDKDRDKAKDKYVRSLWKLF 611
            QQLQQELTKTHSQDIEKLKSQYRALARDSAQAKRKYQEASKDKDRDKAKDKYVRSLWKLF
Sbjct: 121  QQLQQELTKTHSQDIEKLKSQYRALARDSAQAKRKYQEASKDKDRDKAKDKYVRSLWKLF 180

Query: 612  AHHNRYVLGVRAAQLHHQHHHQLLLPGLLRSLQDLHEEMACILKEILQEYLEISSLVQDE 791
            AHHNRYVLGVRAAQLHHQHHHQLLLPGLLRSLQDLHEEMACILKEILQEYLEISSLVQDE
Sbjct: 181  AHHNRYVLGVRAAQLHHQHHHQLLLPGLLRSLQDLHEEMACILKEILQEYLEISSLVQDE 240

Query: 792  VVAIHREMAAAAARIQPEAEYQGFLRQYGSAPDVPPCVTFDESLLEEGEPLEPGELQLNE 971
            VVAIHREMAAAAARIQPEAEYQGFLRQYGSAPDVPPCVTFDESLLEEGEPLEPGELQLNE
Sbjct: 241  VVAIHREMAAAAARIQPEAEYQGFLRQYGSAPDVPPCVTFDESLLEEGEPLEPGELQLNE 300
```

FIG. 2C

```
Query:  972 LTVESVQHTLTSVTDELAVATEMVFRRQEMVTQLQQELRNEEENTHPRERVQLLGKRQVL 1151
             LTVESVQHTLTSVTDELAVATEMVFRRQEMVTQLQQELRNEEENTHPRERVQLLGKRQVL
Sbjct:  301 LTVESVQHTLTSVTDELAVATEMVFRRQEMVTQLQQELRNEEENTHPRERVQLLGKRQVL 360

Query: 1152 QEALQGLQVALCSQAK-------LQAQQE-----------LLQTKLEHLGPGE------- 1256
             QEALQGLQVALCSQAK       LQ + E           LLQ        E
Sbjct:  361 QEALQGLQVALCSQAKLQAQQELLQTKLEHLGPGEPPPVLLLQDDRHSTSSSEQEREGGR 420

Query: 1257 -------------------PPPVLLQDDR----------------------HSTSS 1304
                                PPP+ L+ + +                      HS
Sbjct:  421 TPTLEILKSHISGIFRPKFSLPPPLQLIPEVQKPLHEQLWYHGAIPRAEVAELLVHSGDF 480

Query: 1305 SEQEREGGRTPTLEILKSHISGIFR-PKFSNLYRLEGEGFPSIPLLIDHLLSTQQPLTKK 1481
             +E +G +    L +L    +   F   NLYRLEGEGFPSIPLLIDHLLSTQQPLTKK
Sbjct:  481 LVRESQGKQEYVLSVLWDGLPRHFIIQSLDNLYRLEGEGFPSIPLLIDHLLSTQQPLTKK 540

Query: 1482 SGVVLHRAVPKDKWVLNHEDLVLGEQIGRGNFGEVFSGRLRADNTLVAVKSCRETLPPDL 1661
             SGVVLHRAVPKDKWVLNHEDLVLGEQIGRGNFGEVFSGRLRADNTLVAVKSCRETLPPDL
Sbjct:  541 SGVVLHRAVPKDKWVLNHEDLVLGEQIGRGNFGEVFSGRLRADNTLVAVKSCRETLPPDL 600

Query: 1662 KAKFLQEARILKQYSHPNIVRLIGVCTQKQPIYIVMELVQGGDFLTFLRTEGARLRVKTL 1841
             KAKFLQEARILKQYSHPNIVRLIGVCTQKQPIYIVMELVQGGDFLTFLRTEGARLRVKTL
Sbjct:  601 KAKFLQEARILKQYSHPNIVRLIGVCTQKQPIYIVMELVQGGDFLTFLRTEGARLRVKTL 660

Query: 1842 LQMVGDAAAGMEYLESKCCIHRDLAARNCLVTEKNVLKISDFGMSREEADGVYAASGGLR 2021
             LQMVGDAAAGMEYLESKCCIHRDLAARNCLVTEKNVLKISDFGMSREEADGVYAASGGLR
Sbjct:  661 LQMVGDAAAGMEYLESKCCIHRDLAARNCLVTEKNVLKISDFGMSREEADGVYAASGGLR 720

Query: 2022 QVPVKWTAPEALNYGRYSSESDVWSFGILLWETFSLGASPYPNLSNQQTREFVEKGGRLP 2201
             QVPVKWTAPEALNYGRYSSESDVWSFGILLWETFSLGASPYPNLSNQQTREFVEKGGRLP
Sbjct:  721 QVPVKWTAPEALNYGRYSSESDVWSFGILLWETFSLGASPYPNLSNQQTREFVEKGGRLP 780

Query: 2202 CPELCPDAVFRLMEQCWAYEPGQRPSFSTIYQELQSIRKRHR 2327
             CPELCPDAVFRLMEQCWAYEPGQRPSFSTIYQELQSIRKRHR
Sbjct:  781 CPELCPDAVFRLMEQCWAYEPGQRPSFSTIYQELQSIRKRHR 822   (SEQ ID NO:4)
```

Hmmer search results (Pfam):

| Model | Description | Score | E-value | N |
|---|---|---|---|---|
| CE00287 | CE00287 PTK_Eph_orphan_receptor | 285.3 | 7.8e-82 | 1 |
| PF00069 | Eukaryotic protein kinase domain | 271.5 | 1.1e-77 | 1 |
| CE00292 | CE00292 PTK_membrane_span | 240.7 | 2.1e-68 | 1 |
| CE00290 | CE00290 PTK_Trk_family | 232.7 | 5.4e-66 | 1 |
| CE00291 | CE00291 PTK_fgf_receptor | 190.3 | 3e-53 | 1 |
| CE00031 | CE00031 VEGFR | 149.8 | 6.1e-45 | 2 |
| PF00611 | Fes/CIP4 homology domain | 149.0 | 1.9e-42 | 1 |
| CE00334 | E00334 urotrophin_receptor | 143.6 | 3.5e-45 | 1 |

FIG. 2D

```
CE00286  E00286 PTK_EGF_receptor                          141.3    1.7e-38   1
CE00204  CE00204 FIBROBLAST_GROWTH_RECEPTOR               124.9    8.1e-34   2
CE00288  CE00288  PTK_Insulin_receptor                    110.9    2.5e-29   1
CE00202  CE00202 EPHRIN_TYPE_A_RECEPTOR                   108.3    1.9e-29   3
CE00203  CE00203 ERBB_RECEPTOR                             81.8    2.1e-22   1
CE00549  CE00549 NGFR                                      69.2    7.4e-20   1
CE00201  CE00201 EPHRIN_TYPE_B_RECEPTOR                    57.0    5.9e-15   4
CE00359  E00359 bone_morphogenetic_protein_receptor        26.3    9.4e-07   1
PF00017  Src homology domain 2                             10.4      0.024   1
PF00422  ATP synthase Alpha chain, C terminal               7.7      0.11    1
CE00289  CE00289 PTK_PDGF_receptor                        -33.8    8.2e-05   1
CE00016  CE00016 GSK_glycogen_synthase_kinase            -290.0       1.2    1

Parsed for domains:
Model    Domain  seq-f  seq-t    hmm-f hmm-t     score   E-value
PF00611   1/1       1    94 [.      1   109 []   149.0   1.9e-42
PF00422   1/1     210   234 ..    111   135 .]     7.7     0.11
PF00017   1/1     441   460 ..     60    79 .]    10.4     0.024
CE00201   1/4     497   510 ..    662   675 ..     0.1       17
CE00202   1/3     497   511 ..    680   694 ..     3.2      2.4
CE00202   2/3     534   557 ..    721   744 ..     5.3     0.63
CE00201   2/4     534   567 ..    702   735 ..     4.2      1.3
CE00031   1/2     483   580 ..    868   972 ..     4.5     0.17
CE00289   1/1     489   588 ..      1   109 []   -33.8   8.2e-05
CE00204   1/2     600   636 ..    649   685 ..    68.1   3.5e-18
CE00201   3/4     598   636 ..    766   804 ..    21.3   2.9e-05
CE00359   1/1     495   636 ..    145   299 ..    26.3   9.4e-07
CE00204   2/2     653   692 ..    702   741 ..    56.1   7.1e-15
CE00201   4/4     653   697 ..    824   868 ..    30.5   9.5e-08
CE00334   1/1     490   734 ..    539   803 ..   143.6   3.5e-45
CE00203   1/1     598   737 ..    850   989 ..    81.8   2.1e-22
CE00202   3/3     598   740 ..    827   970 ..    99.5   5.2e-27
CE00290   1/1     491   744 ..      1   282 []   232.7   5.4e-66
CE00291   1/1     491   744 ..      1   285 []   190.3     3e-53
CE00286   1/1     491   744 ..      1   263 []   141.3   1.7e-38
CE00292   1/1     491   744 ..      1   288 []   240.7   2.1e-68
CE00031   2/2     598   744 ..   1056  1203 ..   145.3   1.4e-43
CE00287   1/1     491   744 ..      1   260 []   285.3   7.8e-82
CE00288   1/1     491   744 ..      1   269 []   110.9   2.5e-29
CE00549   1/1     598   745 ..    693   840 ..    69.2   7.4e-20
PF00069   1/1     491   746 ..      1   278 []   271.5   1.1e-77
CE00016   1/1     431   751 ..      1   433 []  -290.0      1.2
```

FIG. 2E

```
   1 CTGGCCACCA GGCTGGCGCA GCCAAGGCCG AAGCTCTGGC TGAACCCTGT
  51 GCTGGTGTCC TGACCACCCT CCCCTCTCTT GCACCCGCCT CTCCCGTCAG
 101 GGCCCAAGTC CCTGTTTTCT GAGCCCGGGC TGCCTGGGCT GTTGGCACTC
 151 ACAGACCTGG AGCCCCTGGG TGGGTGGTGG GGAGGGGCGC TGGCCCAGCC
 201 GGCCTCTCTG GCCTCCCACC CGATGCTGCT TTCCCCTGTG GGGATCTCAG
 251 GGGCTGTTTG AGGATATATT TTCACTTTGT GATTATTTCA CTTTAGATGC
 301 TGATGATTTG TTTTTGTATT TTTAATGGGG GTAGCAGCTG GACTACCCAC
 351 GTTCTCACAC CCACCGTCCG CCCTGCTCCT CCCTGGCTGC CCTGGCCCTG
 401 AGGTGTGGGG GCTGCAGCAT GTTGCTGAGG AGTGAGGAAT AGTTGAGCCC
 451 CAAGTCCTGA AGAGGCGGGC CAGCCAGGCG GGCTCAAGGA AAGGGGGTCC
 501 CAGTGGGAGG GGCAGGCTGA CATCTGTGTT TCAAGTGGGG CTCGCCATGC
 551 CGGGGGTTCA TAGGTCACTG GCTCTCCAAG TGCCAGAGGT GGGCAGGTGG
 601 TGGCACTGAG CCCCCCCAAC ACTGTGCCCT GGTGGAGAAA GCACTGACCT
 651 GTCATGCCCC CCTCAAACCT CCTCTTCTGA CGTGCCTTTT GCACCCCTCC
 701 CATTAGGACA ATCAGTCCCC TCCCATCTGG GAGTCCCCTT TTCTTTTCTA
 751 CCCTAGCCAT TCCTGGTACC CAGCCATCTG CCCAGGGGTG CCCCCTCCTC
 801 TCCCATCCCC CTGCCCTCGT GGCCAGCCCG GCTGGTTTTG TAAGATACTG
 851 GGTTGGTGCA CAGTGATTTT TTCTTGTAA TTTAAACAGG CCCAGCATTG
 901 CTGGTTCTAT TTAATGGACA TGAGATAATG TTAGAGGTTT TAAAGTGATT
 951 AAACGTGCAG ACTATGCAAA CCAGGCCCAG TCTCCAGTGT GGTACCGTTG
1001 CTCCTGCATC GCAGCTGAGG ATAGGGGGCC AGTTAGGCCT ACACAGTGGC
1051 CTGCCTGCCT GGATGTGGGC CCAAGTCAGA AGGCCAAAGT CCTCCAAGGG
1101 GCGGGAGGAT GCGCCAGCCC CTAGTGGAGG AGCTGGTGCC CCTGGGGTGG
1151 GGCTGGTGAC CCCTGGTCCT CAGGAGCTGA GCACTAAACT CCCAAAGTCC
1201 TGGTTTCCAG CAGTGTGAAG AACTGGGCCT ATTGTGTCTT CCTGGGCTGA
1251 AGTGATCTGG TCGCCACAGG CTATAGGGCT GAGGCCTAAG GTGGAGGGAG
1301 GCCTGACTGA ATCAAGATGA CTTCTTGTGG GGAGCCTGAG TCCCAAATGG
1351 AAAACTCCAC GCCTGTCCGC TCCCCAACCC CTGCCCCTTG ATTTCCCCAG
1401 GTCTCCCTTG GGACAGGAAG CCCCTGCCTG GGGGTAGGAG GATGGGGACA
1451 AAACCACTAG GATCTGTATC CGAGAAGCAG TCTCTGTTCG GGATATTTAC
1501 TTGGAAATTT TATTCAAATG GAAGCTGGCG CCTGAGCCTC TCCTTAGGGA
1551 ATTCCGTGAG GTGGGGAGGG CTGGGACCAG GGTTCCCTCT TTCTCTTCTG
1601 CGGTGGCCCT GGCCTGGTGC TAGGACTGCG CGCCTCCCCT CAGTACCCGC
1651 GGACACCCTG GGCTTCCCTG GGCCCAGCAT CTGCCTGGGG CCTCGCCCTG
1701 GGCTCCCCCT CCTGACCCCC ACCTTGCGCC CCTTCCCGGT GTTCCCGGGG
1751 CGCTGCCGGG CCCTGGGGCC TGCGGGGCGC GGGCGGCTCT TGGCTGGGCC
1801 ATTCTTTCCC GGCCCCCTCC TCCCTTCCGT TTCCGTGGCC GTGCGGCCGG
1851 CTAGAGGCTG CGGCCCAGCG CGGAGCAGGG GGGCTGGCAG GCGTCGGGAC
1901 GGTCGGGCCG GTCCCGCCCG CCCCTTCCCC TCCACAGGCC CGCCCCGGGG
1951 CCTGGGCCAA CTGAAACCGC GGGAGGAGGA AGCGCGGAAT CAGGAACTGG
2001 CCGGGGTCCG CACCGGGCCT GAGTCGGTCC GAGGCCGTCC CAGGAGCAGC
2051 TGCCCGTGCG GGTACCTCTA GCCCCGGGGC CTGGAGGAGC GGTGGGAGCT
2101 GGGGGCGCGG CAGGCAGGGG CAGAGCAGGC GTTCCGAGGG CCAGAGACCC
2151 ACCCAGGTGG GGGTAGGGGC CGCGGAAGGG CGGGGATGGC CGCAGGGGCA
2201 GGGCTCAGGC TGTGGGCGCC TGAGGCTTCA GCTGGGGCAG GCTTGGCCTG
2251 TCGAGGACCT GGGCAAGGGT GTCCCTGTAA GGGGTGGTGG GTGGAAGGGC
```

FIG. 3A

```
2301 CTGGGGAGGG AGGCTCCAGG TTGGCTCCTG TTCCCGAACG TGCGGAGGAG
2351 ACCCTGACGC TAAGGAAGCA ATGAGGGCCA GTCCCCAGGC CAGGCTGCTG
2401 CTGGGTACCC ATGGCTGCGT GTGAGCGAGG CAGGACCCCA CCTCCTCCCC
2451 GTCTGCAGTC CATCCTGACC CTACAGTCCC CAGCCTCCTC GTCCCATGCC
2501 TCCGTCTCCA GCTGCTGCCT TGCCTCCAGG GATGGCCCCT TTTCTGTCCC
2551 CAGAACAGCA CTATGGGCTT CTCTTCTGAG CTGTGCAGCC CCCAGGGCCA
2601 CGGGGTCCTG CAGCAAATGC AGGAGGCCGA GCTTCGTCTA CTGGAGGGCA
2651 TGAGAAAGTG GATGGCCCAG CGGGTCAAGA GTGACAGGGA GTATGCAGGA
2701 CTGCTTCACC ACATGTCCCT GCAGGACAGT GGGGGCCAGA GCCGGGCCAT
2751 CAGCCCTGAC AGCCCCATCA GTCAGGTGGG TCTCTATGGG ACTCTGGTGG
2801 GTGCTGGCGT ATCTGCCTTC TCCTTCCTCT CCTGGGGGCC CTCTGGGGCA
2851 GTGGCTGGAG ATCTGGCAGG CCAATGCTTG GGAGCCATTG TGCCCCCCTC
2901 CCTGCCTCCC CCATCTGTGC TGTATAGTCC TGGGCTGAGA TCACCAGCCA
2951 AACTGAGGGC CTGAGCCGCT TGCTGCGGCA GCACGCAGAG GATCTGAACT
3001 CAGGGCCCCT GAGCAAGCTG AGCCTGCTCA TCCGGGAACG GCAGCAGCTT
3051 CGCAAGACCT ACAGCGAGCA GTGGCAGCAG CTGCAGCAGG AGCTCACCAA
3101 GGTGAGCGGG CAGCACTGGG GCTTCGGTCA TTTCTGTCTA AATTTTGAGC
3151 CTCGAAGGGG TTGTTTTGCA CAAGAGGCCC TGGATTCACT GGGGAAGTGT
3201 AAGTCCCTGA CCGCAGGCCT GGCTTGCTCT AACCTTGATG TAGCTTCCTC
3251 TCTTCCTTCC CCTACGTTGA GCTGGCTTGC AGCAAGGCCT CTCTGTGCTT
3301 TTTCTGTGCC TGGGCAAAGT GCTGGGAGTG TAAGGATGAG TGACCGGTCA
3351 CGTGCCTGGG AGAAGCTCAG AATCGGTACT CGCCTCCACA CTGTGCCATC
3401 TGGCTCTGGG TTCTGAGAGT CAGGGAGAGG AATGAGGGTC AGTCTGTTTG
3451 CCTTCGACCT ATGCAGCCTC CTCTCAGGGC CCCAGAGACT GGGCAGCAGC
3501 ATGGCCCCCC GAAGGTCGAG GACTCGGGCC GTGAAGTCAG CCTGCCTAGG
3551 TTTGAATCCC ACCCAGCTCC TCAGTCTAGA GGCTGTGTGA TTTGGAACTA
3601 TTTATCTGGG AGCCTAGTGC CCCCATTCAG TGTGCTGGTC ACCCTCCCTG
3651 CACCACACCC CTTCCTCAAG TGCAGAGCCC AGCCTTGCCA TGGACCCACA
3701 GCGGCCCCTG GTGGCCACCC TGGCCCCATT CCTCGCCCCA AAAGATCATC
3751 TGATTCAAGG GTGGGCCCAT TTTTATAAAG TTTTGCTGGA ACACAGCTAT
3801 GCCCCTTTGT TTTCATATTG TCTGTGACTA CAATGACAGA GTTGAGTAAT
3851 TGTGACAGAG GCTCTATGGC CTACAAGCCT AAAATATTTA TTTACTATCT
3901 GGCCCTTTAA GAAAAAGACT GATCTAGTCG AGGAATCTAG CTCAGTTACA
3951 GATGGGGAAA CTGAGGTTGG GCGCTTGCCC AACATATCCC AGCACATAAA
4001 CAGGAGAACT GGGACGAGAA CACTGATCTC GGGCTGTCAT CTATTCCTAC
4051 TGCCAAGAAC ATAATTTGCA GGACCCAGTG CAAAGTGAAA TTGTGGGGGT
4101 CTTTGTTAAA AGATTGCTAG GAATTTCCAG GTGGCAATAA TGGAGAATGA
4151 AACCAAGCAC AGGGCCCTTC TACATGTGGA GCCCCGTGTG ACTGCACAGG
4201 CCGTGCACAC CTGCAACTGG CCCTGCCTGC CACCAGGCTA CCACTGTCAG
4251 TCCAAGGAGG GACCGTTGTA GCCTGTAGTC TACCTCTTTG CCTCCCCAAG
4301 GGGTCTGTCT TCAACAGGCT CTCTGATCTT TGACTCTCAC GTCAGCAGCC
4351 AGCTTTCCCA GAAGTCTCCA GGTGCTCCTT GCCTGACGAC AGGACCTTTC
4401 CAGGGCTTCA CCCCAGGCAA GAATCTTCCA CAACTGGGGA CCTGCTGCCC
4451 CACACTGGCC TCTCCTCTCT CCCTAGACCC ACAGCCAGGA CATTGAGAAG
4501 CTGAAGAGCC AGTACCGAGC TCTGGCACGG GACAGTGCCC AAGCCAAGCG
4551 CAAGTACCAG GAGGCCAGCA AAGGTTCGTG GCTTCCCTTG CTGGCAGGGA
```

FIG. 3B

```
4601 GGGAATCCGA AGCCAGTGCT GACCTGTCCT TGGGTACCCA GAGAGTGGGG
4651 GCTGCCTGGG CCTCCATGCT GTCATCTATA CCCCTTGCCC CCCTTCTGGC
4701 AGACAAGGAC CGTGACAAGG CCAAGGACAA GTATGTGCGC AGCCTGTGGA
4751 AGCTCTTTGC TCACCACAAC CGCTATGTGC TGGGCGTGCG GGCTGCGCAG
4801 CTACACCACC AGCACCACCA CCAGCTCCTG CTGCCCGGCC TGCTGCGGTC
4851 ACTGCAGGAC CTGCACGAGG AGATGGCTTG CATCCTGTAA GCCCGCAGCC
4901 CCGTCCCCTG GCCCCCACCC TTGAGCAGCC CTAAGCCCAG CCATCAGGCC
4951 CAGAGGCAGG ACCCAGAAAA TCCATTGCTG GGAAGGTGCT GGCCATGTAA
5001 CCACATGAGA ACGGGACCTG GGCCAAGGAT TGGAAACAGG CAACTTACCT
5051 CTGAATTACA CTATTCCAGG GTCTCATTAT TCCAGGGTTT TATTACATTC
5101 ATTGAGCACT GTTCTGGGCT CTGGATTATA CCAGAGAACG ATGGTAGACA
5151 AAAACATCTG TCCTCAGGGA TCTTTCGTGT TAGTGGAGTG AGAATGTGAG
5201 GAGCACTAAG AGCCATGGAG AAAAATAAAG CAAGAGAAGT GGATCGGGAC
5251 CTGGGAGCAC GGAGGCAAGG GAGGAGGTGA CAGTTGTCCA TAGAGTGATC
5301 TGGAAAGCC TCTTGAGAGG TGACATTCAA AGAGGCCCCT GAGAGGGTA
5351 CGGGAGTGAA TCATGGGGCT ATTTGGAGAA AGACCATTCC AGAAAGGAGG
5401 ACAGCAATTA CACAGGCCTT GAGGTAGGAG AGTACCAGGG ACTAATAGCC
5451 AGGAACCAGT GGTGCCTCTG AGAGTGAGGG AGGGGAGAG TCATACACGA
5501 GGCTGGAGGA GGCAGGCGTC AAGGGCTACT GGGTGATAGA AGGTCTAGCA
5551 GGGCCATGGT GAGGACTTTG GCTCTGGGTG AACAAGAATG CATGATCTG
5601 ACCTCTGTTT TTTTGTTTCA TTTTGTTTTA ACTTTTTTTG AGTCAGAGTC
5651 TCGCTCTGCC GCCCAGGCTA GAGTGCAGTG GCATGATCTC GGCTTACTGC
5701 AACCTCCGCC TCCCAGGTTC AAGTGATTCC CCTGCCTCAG CCTCCCGAGT
5751 AGCTGAAACT ACGGGCATGC GCCACCACAC CCAGCTAATT TTTGTATTTT
5801 TAGTAGAGAC GGGGTTTCAC CATGTTGCCC AGGCTAGTCT CTAATTCCTG
5851 GGCTCAAAGC GATTTGCCTG CCTCTGCCTC CCAAAGTGCC GGGATTACAG
5901 GCATGAGCCA CCATGCCCAG CCCTGACCTC TGTTTTAATA AGGCCACTCT
5951 GGCTGCTGTG CTGCAAATAG ACTTCAGGGA GCAAGGACAG AAGCTGGGAG
6001 GCCAGAGAGC AGGCTGCTTG CCATAATCCA GATCCAAGCT TTTGGCCAGC
6051 TAGGACGGGG AGGTAGCAAT GGAGGTGAGG CGCGGTCAGG TCCTGGGGCA
6101 GGTCCTGGAA GGTGAAGCCA GTGGGATTTC CCTATGGATT GGAAGTGGGG
6151 CGTGAAATAG AGGAGTCAGG GGTCACTCTG GGGATTTGGC CTGGAGCAGC
6201 TGGAAGATGG AGTGGCTGTT AACTTATGTA GGGAAGGCTG TGGGAAGAAG
6251 AGGTTTAGGA GACAAGGATA GCAGTTCATT TATTTATTTA TTTATTTATT
6301 TATTTATTTA TTTATTTAGA GATGTAGTCT CATTCTTTCG CCAGGCTGGA
6351 GTGCAGTGGC GCGATCTTGG CTCACTGCAA CCTCCACCTC CCAGGCTCAA
6401 GCGATTCTCT TGCCTCAGCC TCCCAGTAG CCAAGTAGCT GGGACTACAG
6451 GCATGTGCCA CCATGCCTGG CTAATTTTTG TATTTGCTTT TTCAGTAGAG
6501 ATGGGGTTTC ACCACGTTAG CCAGGCTGGT CTCGAACTGA CCTCAGGCAA
6551 TCCACCCGCC TCGACCTCCC AGTGTTGGTA TTATAGGCGT GAGCCACTGT
6601 GCCTGGCCCA CTGGATCCTT ATTACAACTG CCAGTGTCCC TCTTATATAT
6651 ATCAGGAAAT AGAAGATTAG GGAGAGGTTA AATAATTTGC CTAGAGTGGC
6701 ATGGCTAGCT CGAAGTGAGG CAGGGGTCAA CCCCAGCCCT GACTCCAAAC
6751 CCAGGGTCCT AGGCCTGAAC TGCCCAGCCT TGCCCAGCCT GAGGCTCCCC
6801 TGACTGGGGA TCCCGTCTCG GGGCAGGAA GGAGATCCTG CAGGAATACC
6851 TGGAGATTAG CAGCCTGGTG CAGGATGAGG TGGTGGCCAT TCACCGGGAG
```

FIG. 3C

```
6901 ATGGCTGCAG CTGCTGCCCG CATCCAGCCT GAGGCTGAGT ACCAAGGCTT
6951 CCTGCGACAG TATGGGTAAG CCCCGTCCTT GCTCCTGCTG GGCCCAGGGC
7001 TGCTGGCCTG TCCACTGACG GGGCGCTGTC CCCCACAGGT CCGCACCTGA
7051 CGTCCCACCC TGTGTCACGT TCGATGAGTC ACTGCTTGAG GAGGGTGAAC
7101 CGCTGGAGCC TGGGGAGCTC CAGCTGAACG AGCTGACTGT GGAGAGCGTG
7151 CAGCACACGT GGGTGGTGGC TTTGCACCTG GGCTGCGGCG GGCTCCCAG
7201 CAGACCACGA GTGTTTATGT AGGCAGGGCT AGGTCGTGGA GACTGTCCAC
7251 ACAGAGCTGT CACCAGGTGG CCGGGCTTGC TTGGCTCTAC AGGGATGCAC
7301 TGGACCTGGG TTGAGGGGGC AGGAGGGCTC GGTTCTAATG CTGCCCTTCT
7351 CTTGGGTGCA GGCTGACCTC AGTGACAGAT GAGCTGGCTG TGGCCACCGA
7401 GATGGTGTTC AGGCGGCAGG AGATGGTTAC GCAGCTGCAA CAGGAGCTCC
7451 GGAATGAAGA GGAGAACACC CACCCCCGGG AGCGGTGAGT GGGCCCCTGC
7501 CTGCAGCAGC CTCCTGGGCC TCCCTCCCTC CTACCTACCC TAACTGCTGC
7551 TGGCTAGCCG CCGCAGACCG AGCCCTTATT CTTCATCCAC CCTCCCACCC
7601 GCCCCTGCCT GCAGGGTGCA GCTGCTGGGC AAGAGGCAAG TGCTGCAAGA
7651 AGCACTGCAG GGGCTGCAGG TAGCGCTGTG CAGCCAGGCC AAGCTGCAGG
7701 CCCAGCAGGA GTTGCTGCAG ACCAAGCTGG AGCACCTGGG CCCCGGCGAG
7751 CCCCCGCCTG TGCTGCTCCT GCAGGATGAC CGCCACTCCA CGTCGTCCTC
7801 GGTGAGCTGC CCCATCCGCG CCGCTGCCC GCCACCGGCC TGCCCACCTG
7851 GGGCTGCGCT CCTCATTTTC GCCCTCCCCC TCCCTAAGCC TGGCCACCCG
7901 CTGACGTCTG TCCCTGGCCT CAGGAGCAGG AGCGAGAGGG GGGAAGGACA
7951 CCCACGCTGG AGATCCTTAA GAGCCACATC TCAGGAATCT TCCGCCCCAA
8001 GTTCTCGGTG AGTGGCGCCC AGCCTGGGCC CCCCTACTGT TGTGTTTCGA
8051 GTTTAATCAC TGGGATGTCC TAGAGAGGAG GCTCTGCCCA GGCTGCTTGT
8101 ATTGGGAAGT TCCTCTCTTC CCTGGGATTC CAGGCTGCAG ATGTCCCCAG
8151 ACCCTGCCCC TGTGACCCCT CCCTTTCCAT CGCCCCAGTG TGCTAAAGGG
8201 ACCAGCAACC TCGACTATTC CATGGCTCTC CCTGCTTCAG GAGCGGTTGG
8251 GGGCCTGTGG CCTGGAGGAG GAGGCACCAG CTTGGTTTGG GGTCTTCCTG
8301 CCTGGGCTTC CCTTCCCAGC TCTGCCCAGC GTGAGCCTGG GCCAGTCCAG
8351 TGCCCACTCC AGGGGCCTGT GGATGGCTCT GCATGCCACT CCATGGTTGT
8401 AAGGGCTGAG GGCATATAGG GGGGAGAGAG AGACCCCCGG CTGCCCCCAC
8451 GGCCTCTTCA ACAAGGTGGT TAAGTGACTC CTCCTCGATC CTCCCTTGCC
8501 CAGCTCCCTC CACCGCTGCA GCTCATTCCG GAGGTGCAGA AGCCCCTGCA
8551 TGAGCAGCTG TGGTACCACG GGGCCATCCC GAGGGCAGAG GTGGCTGAGC
8601 TGCTGGTGCA CTCTGGGGAC TTCCTGGTGC GGGAGAGCCA GGGCAAGCAG
8651 GAGTACGTGC TGTCGGTGCT GTGGGATGGT CTGCCCCGGC ACTTCATCAT
8701 CCAGTCCTTG GATGTGAGTG GGCTGGGAC CCGAGCCTTC CAGGCCTCAC
8751 TCTTCCCCTC CCTTCCCTTC CCCAAGGGAA ATGGCCTTTC AGGGTAGGGG
8801 GTAGCTGCCA GGTCTTGGAT GCCTCCCTAG CAGGGCTGGC TGGAAGGGGC
8851 CACAGAGACC ACCCTGTCCC TGCAACAAAA TAGAGGCTTA AGTGTGAGTC
8901 CTCCCCTGGT GGGGCAGCAG GATGTCATGT GCCATCAGAT GGCATCTTTT
8951 CTGGAGGTCT CTCTGCCCCT GGTCCTGGGC AGGCCCTTTC TCCCCTGCTG
9001 CTCTCCCTTT CCCCCTCCCA GGGCTCACGC CCCTCAGAA TGGAGGCTGC
9051 TGACCCCGGG TCCCCTGCCC TGCAGAACCT GTACCGACTG GAAGGGGAAG
9101 GCTTTCCTAG CATTCCTTTG CTCATCGACC ACCTACTGAG CACCCAGCAG
9151 CCCCTCACCA AGAAGAGTGG TGTTGTCCTG CACAGGGCTG TGCCCAAGGT
```

FIG. 3D

```
 9201 GAGCCTGCAC CCAGCCTGGC CCATGCCACC TGTGGCAGGG CTTGGGGAGT
 9251 GTGGGTCAGG CCCACCCAGC GTCTGAGCAG AAAGGGCTTT CCAGGCCCTC
 9301 CGTCTACATA CAAGATGCAG AGTGAGTGAC CCTCAGGGCC AGCCTTGCTC
 9351 TAGGTTTGGA ATGTCAGGGC CACTCCTATG CCATGGGCTG TACACACCAG
 9401 GTTGGTGCTT ACCTGGTCAG GGCACCTGCC TGGACCCCGT AGTCATCTCA
 9451 GTGTGCTCCC CACGTGGTCC CACCCCTGGT CACATATGGA GGCGCCAAAA
 9501 AATGGAGGAC ACAGCCCTTC TAAGGGCCCA GCACCCCTTT TCTTCAGACT
 9551 TCTGATCCCC TGTCTCCTCT CTTCCCCAGG ACAAGTGGGT GCTGAACCAT
 9601 GAGGACCTGG TGTTGGGTGA GCAGATTGGA CGGGTGAGTG CGCCTCTGCT
 9651 GGCCTCCTTG TCGCTGGCGA CTTCTCCTGA GTCGCGCCTG GGCCCCTGC
 9701 CCTACCACCC AGAAACCTCC CTGCCCCATC TGATTCCCCA CTTGTACCCC
 9751 GACTCCCTGC CCAGCCCCCA CCACACACCA TCCTCCAGGA AACGGGACAG
 9801 TACCTACGCT GAAAACTCCC AGCAGACAGC TCTGCCAGCA CCCTGACCTC
 9851 ATCACCCCCA CCCAGGCCGC CCCCATCGAG CTCTTGTGTG CACGCAGGGA
 9901 GACACCCTGT TACTGTAAGC CATAAGATAC CTGTTTAGGG AAGAAGTCAC
 9951 TGTCCTAAAA ATCAGAATGC TTTTCAAACC CAAGGGAGAG TGATTTTTGG
10001 ATTTCCATGT CACTTCTCTC AGGAAGGGTG GCACATCGGA GGCAACTTTC
10051 CCTGCCTGCC CCATGTGCTC TCTAGGTTCC CCAGCGAGGG TCAAACTCCC
10101 AGAGAGCCTG GGTGGAGGGG TCCGAACACG GGGGCCCCTC ACCCAGGGGT
10151 AGGAAGCAGA ATGGGTAGGA AGCGGAGAAG AGAACTGCGG GACTGGGAAG
10201 GCCGTGGTAG GAGCCCAAGA CCGTTTCAGG GGAACTTTGG CGAAGTGTTC
10251 AGCGGACGCC TGCGAGCCGA CAACACCCTG GTGGCGGTGA AGTCTTGTCG
10301 AGAGACGCTC CCACCTGACC TCAAGGCCAA GTTTCTACAG GAAGCGAGGT
10351 GGGTGATAAA CTAATGATCA CCACGGGTCC CGCATACACA GAGGTTACAC
10401 TGCATGGCAC AGTGTGAAGT GCTTGACCAC CGTGGTGGTG TTTAGTCCTC
10451 GAGGCCCCCC ATTGCGGGTA GTACCCCCTT ATAGTGCCGA AGGGTAGAGG
10501 CTGCCCCAGG TCACACGTCC GGGTCTGCTG GCCTTGGAGG CCAAGCTCTT
10551 CTCCCATCAT CCCTGGGGGG CCCTGGGGAG GCGGGCCTGG CCACGTAGAT
10601 CCTGAGCAGC AGTGCCCTCC AGGATCCTGA AGCAGTACAG CCACCCCAAC
10651 ATCGTGCGTC TCATTGGTGT CTGCACCCAG AAGCAGCCCA TCTACATCGT
10701 CATGGAGCTT GTGCAGGGTG AGCGCGGGGC GCTGAGCTCC AGGTAGGGCG
10751 CGCAGCCTGG TCAGGTGGCA GCCTTACCTC AGGAGGCTCA GCAGGGGTCC
10801 TCCCCACCTG CAGGGGGCGA CTTCCTGACC TTCCTCCGCA CGGAGGGGGC
10851 CCGCCTGCGG GTGAAGACTC TGCTGCAGAT GGTGGGGGAT GCAGCTGCTG
10901 GCATGGAGTA CCTGGAGAGC AAGTGCTGCA TCCACCGGTG AGTGGGCGGT
10951 GGCCACGGGC CCTGCCAACA CCCCCGACCA GAGTCAAGAG GTACCTATAC
11001 CCCTAGGGCC CCCCGCTGGA CCATCAGGCA TCAGCTCCAG AGGGGGAGTT
11051 GGCCTCTGTG GTAGACAGGG GTGCCCAGGG CCGGGAGCAG CTTTTGTCCT
11101 TGGCTTTCCT AGAGTGTTCA GCCAGGGCTG GGCAGGCGAC TGTTGGCCAA
11151 ATGAGCCCCT GCCCTGTCTC ACCCAGGGAC CTGGCTGCTC GGAACTGCCT
11201 GGTGACAGAG AAGAATGTCC TGAAGATCAG TGACTTTGGG ATGTCCCGAG
11251 AGGAAGCCGA TGGGGTCTAT GCAGCCTCAG GGGGCCTCAG ACAAGTCCCC
11301 GTGAAGTGGA CCGCACCTGA GGCCCTTAAC TACGGTACCT AGTCCCTGTC
11351 TACCCTGGAC TCCATGGCCA GAGGCCAGGC CTGGGTCCTG CCGGCTGCCT
11401 CGCCCTGGCC CCAGGGAGGG TGCACTCACG CTGCCTCACC TCCTCGCCTC
11451 CTCTGCAGGC CGCTACTCCT CCGAAAGCGA CGTGTGGAGC TTTGGCATCT
```

FIG. 3E

```
11501 TGCTCTGGGA GACCTTCAGC CTGGGGGCCT CCCCCTATCC CAACCTCAGC
11551 AATCAGCAGA CACGGGAGTT TGTGGAGAAG GGTAAGCACC CTGTGATGAC
11601 AGCAGCCTCA GGCTGCACCC TCTTCCAGAT GCTCCAGCCG GACTCTTCTA
11651 ACTCCCTTAA TGCCAACCTT CCCACCAGGC AGAATAAGAA TAACCTGGCC
11701 AGTTGCTCAC GCCTGTCATC CCAGCACTTT GGGAGGCTGA GCTGGGTGGA
11751 TCACTTGAGC CCAGGAGTTC AAGATCAGCT TGGACAACAC AGTGAAACTC
11801 CATCTGTACA AAAAATACAA AAATAGACTG GGCACGGTGG CTCACACCTG
11851 TAATCCCAGC ACTTTGGGAG GCCGAGGCAG GTGGATCACC TGTGGTCAGG
11901 AGTTTGAGAC CAGCCAGACC AACATGGTGA AACCCCATCT CTACTAAAAA
11951 TACAAAAATT AGCCAGGCAT GGTGGCACGT GCCTGTAATC CCAGCTACTT
12001 GGGAGGCTGA GGTGGGAGAA TTGCTTGAAC CCAGGAGGCG GAGGCTGCAG
12051 TGAGCCGAGA TTGTGCCACT GCACTCCAGC CTGGGCGACA GAGTGAAAC
12101 TCCATCTCAA AAAAAACCAA AAACAAAAA ATACAAAAAT TAGCTGGGTG
12151 TGGTGACATG CGCCTGTAGT CCCTGCTACT CGGGAGGCTG AGGTGGGAGG
12201 ATCACTGGAG CCCGGGAGGT GGAGGTTGCA GTGAGCTGAG ATCATGCCAC
12251 TGCACCCCAA CCTGGGTGAC AGAGAGAGAG AGAGACCTTG ACTCGAAAAA
12301 GAAAAAAACC TGGGCGCAGT GGCTCACGCC TGTAATTTCA ACATTTTGGG
12351 AGGCTGAGGA AGGTGGATCA CTTGAGTCTA GGAGTTTGAC ACTAGCCTGG
12401 CCAACATGGC AAAACCTGTC TCTACTAAAA ATACAAAAAA TTAGCGAGGT
12451 GTAGTGGTGC AAGCCTGTAA TCCCAGCTAC TTGGGAGGCT GAGGCACAAG
12501 AATCGCTTGA ACCTGGGAGG TGGAGGTTGC AGTGAGCTGA GATCACACCA
12551 CTGCATTCCA GCGTGGGTGA CAGAGCAAGA CTCCATCTCA GAAAAAGAAA
12601 AAAAAAAATA GAATATCCCT GTAGCTACTA CTGAGTGAGC ACCTGGTCTG
12651 TGCTAGGTCA CATGTTATTT CATTTGCTCA TCACTACATG TGTGGTAGGG
12701 ATTAATATGT CCCTTTCTCA GATGGAAAAA CAGGCTGGCA GAGGGGACAC
12751 AGCTAGCACG TGGTAGGATT AGGATCAGAA GCCAGGCCTC TTTGTCCTTT
12801 GGGCCCTTGG TGGAGAACAG TGCATCCTTC AGAACAGTGC ATCTTAAGCA
12851 GCTCCTATGG CTCATGGTAT CCCCCAGAGT CTGCCGAGGA CCCTCAAACT
12901 CCCTCCTCAT GCCTGGTGTG CTGTGCCTCT CCTCACAGGG GGCCGTCTGC
12951 CCTGCCCAGA GCTGTGTCCT GATGCCGTGT TCAGGCTCAT GGAGCAGTGC
13001 TGGGCCTATG AGCCTGGGCA GCGGCCCAGC TTCAGCACCA TCTACCAGGA
13051 GCTGCAGAGC ATCCGAAAGC GGCATCGGTG AGGCTGGGAC CCCCTTCTCA
13101 AGCTGGTGGC CTCTGCAGGC CTAGGTGCAG CTCCTCAGCG GCTCCAGCTC
13151 ATATGCTGAC AGCTCTTCAC AGTCCTGGAC TCCTGCCACC AGCATCCACA
13201 CTGCCGGCAG GATGCAGCGC CGTGTCCTCT CTGTGTCCCT GCTGCTGCCA
13251 GGGCTTCCTC TTCCGGGCAG AAACAATAAA ACCACTTGTG CCCACTGAAC
13301 ACTCCTGGCA TGTGCACTCC TCTGGAAGGC AGGTCTCAGA AGGCACAAGT
13351 GCCGGTATGG TGGCCTTGGG GAAGGAGGAG GACAGGCAGT ATGCATGGGG
13401 CAGAGCTGAC ATGATTTAGT AGCAGCTGGA TGTGAGACAT GCGGAAGGCG
13451 GGGGAGAGAT CAGGATGATA TACAGGCTAT GGCCAGATGG CGGTGTCATC
13501 CCCTGAAATA GGATTATAGG AAGAGGATCA GAGCTTCGAG GAGGATGTTG
13551 AGTTTAGAGA TGTTGCATTT TATTGGAGAT AAAAGTGTGG GTGAAGCCAG
13601 GTGTGGTGGT AGACACCTGT AGTCCCAGGT ACTTGGGAGG CCAAGGCATG
13651 TGGATTGCTT GAGCCTAGTT TGAGACCAGC CTGGGCAACA TGGCAAAACT
13701 CCATCTTTAC AAAAACAAAA AACAAAAAAC AAAAAACCAA GTAAAATTAG
13751 CCAGGCGTGG TGGCACACAC CTATAGTCCC AGCTACTCAG AAGGCTGAGG
```

FIG. 3F

```
13801 TAGGAGGATC AATTGAGCCT CGGAGGTCGA GGCTGCAGTG AGCTGTGATC
13851 ACACCACTGC ATTCCAGCCT GGGCAACAAA GCGAGGCCCT GTCTCAAAAA
13901 TAAGTAAATA AAAATAATAA ATAATTAATT TAAAATGTAG ATGAATAGGT
13951 CTGGAAGCCC AGATGGAGAT GAAGGCTGGC AATAGATGTG TGAATCATTG
14001 GCTTATGAAT ATTAGAGAGT AGCTGACACT ATGGATGCGT ATAACACTCG
14051 CATAAAATTC AGGAGGAGAT GAGAAGAGAG TTCCACTCAA AGAAGACTGA
14101 TGTGGCTGAT GAGGAAGAAA ATGCTTTTGA GGGAGTTGTT TCTCAAGATG
14151 AATTTATTGA GGAATAAGAT GGCAGACTGG GGAGCCTTCA CCTCCTCCCC
14201 TAAGTCCCAG TGAAACCTAA AAAGTCATCT GAAATATTAA CATCACCAAA
14251 AGCGAAGTTT GAGAAGATAA GGAAGTATGA ACATAACTAA AAAACAAAGT
14301 GGGAAACATT TGTAATACAG AACAGGGCAA TGAAAACCTT GAAGTAAAAT
14351 GGCCATCCCT CAAGAAAGTT CAGGAAATAG TTAACATCAG CTGGGTGCAG
14401 TGGCTCACAC CTATAATCCC AGCACTTTGG AAGGCTGAGG CAGGTGGATC
14451 ACCTGAGGTC AGGAGCTCGA GACCAGTCTG GCCAACATAG TGAAACTCCG
14501 TCTCTGCTAA AAATACAAAA AAAATTAGCC AGGCGTGGTG GTGTGCACCT
14551 GTAATCCCAG CTACTCTGGA GGCTGAGAAG GGAGAATTCC TTGAACCGGG
14601 GAGATGAAGG TTGGAGTGAG CAGAGACCGC GCCATTGCAC TCCAGCCTGG
14651 GCAACAAGAG CGAAGAACAA AACTATGTCT CAAAAAAACA AAACACAGCA
14701 AACAAAAATC TATTTTGAAA GAGATGAGAG TGAGCCATAT AACTTGTTTA
14751 AACAAAAGGA AGTTGTGTTG TCGTGTAATT AAATGAAAAT ACTAGGAAGT
14801 GAAATAATAC CTCCAATGGA AATGGTAGAA AGCAGAACTG AAAAACTTCT
14851 GCTAGGTAGG ATATGGTAGG TCTCTGCACG CCACCACTCC CATTGCAACC
14901 GCTAGGGAAA AAACAGCTAA GATGAAAATG TCTTTTTTTT TCTTTTTTTT
14951 TTTTTTTTGA GATGGAGTCT CGCGCTGTTG CACAGGCTGG AGTGCAGTGG
15001 CGCGATCTCA GTTCACTGCA ACCTCTGCCT CTCGGGTTCA AGCGATTCTC
15051 CTGCCTCAGC CTCCTGAGTA GCTGGGATTA CAGGCACGCA TCACTCACGA
15101 GCGGCTAATT TTTGTAATTT TAGTAGAGAC GGGGTTTCAA CATGTTGGTC
15151 AGGCTGGTCT CAAACTCCTG ACCTCAAAGT GACCCGCCCA CCTCGGCCTC
15201 CCAAAGTGTT GGGATTACAG GGATGAGCCA CCACGCCTGG CCGAAATGTC
15251 TTATTTTTAA AAAGAATGAA GAGTGGTCAC AGAAATAAAG ACTGAAT  (SEQ ID NO:3)
```

FEATURES:
Start:    2563
Exon:     2563-2775
Intron:   2776-2927
Exon:     2928-3101
Intron:   3102-4476
Exon:     4477-4573
Intron:   4574-4702
Exon:     4703-4886
Intron:   4887-6827
Exon:     6828-6965
Intron:   6966-7038
Exon:     7039-7158
Intron:   7159-7361
Exon:     7362-7484

FIG. 3G

Intron: 7485-7614
Exon: 7615-7801
Intron: 7802-7923
Exon: 7924-8007
Intron: 8008-9075
Exon: 9076-9198
Intron: 9199-9579
Exon: 9580-9633
Intron: 9634-10229
Exon: 10230-10348
Intron: 10349-10622
Exon: 10623-10717
Intron: 10718-10813
Exon: 10814-10937
Intron: 10938-11176
Exon: 11177-11334
Intron: 11335-11458
Exon: 11459-11581
Intron: 11582-12938
Exon: 12939-13078
Stop: 13079

CHROMOSOME MAP POSITION:
Chromosome 15

ALLELIC VARIANTS (SNPs):

| DNA Position | Major | Minor | Domain | Protein Position | Major | Minor |
|---|---|---|---|---|---|---|
| 28 | C | T | Beyond ORF(5') | | | |
| 847 | A | G | Beyond ORF(5') | | | |
| 2159 | G | C | Beyond ORF(5') | | | |
| 2484 | C | T | Beyond ORF(5') | | | |
| 2577 | T | C | Exon | 5 | S | S |
| 2808 | - | T C | Intron | | | |
| 2922 | G | A | Intron | | | |
| 4312 | C | T | Intron | | | |
| 4903 | G | A | Intron | | | |
| 5193 | A | G | Intron | | | |

Context:

DNA
Position
28  CTGGCCACCAGGCTGGCGCAGCCAAGG
    [C,T]
    CGAAGCTCTGGCTGAACCCTGTGCTGGTGTCCTGACCACCCTCCCCTCTCTTGCACCCGC

FIG. 3H

```
       CTCTCCCGTCAGGGCCCAAGTCCCTGTTTTCTGAGCCCGGGCTGCCTGGGCTGTTGGCAC
       TCACAGACCTGGAGCCCCTGGGTGGGTGGTGGGGAGGGGCGCTGGCCCAGCCGGCCTCTC
       TGGCCTCCCACCCGATGCTGCTTTCCCCTGTGGGGATCTCAGGGGCTGTTTGAGGATATA
       TTTTCACTTTGTGATTATTTCACTTTAGATGCTGATGATTTGTTTTTGTATTTTTAATGG

847    ATGCCGGGGGTTCATAGGTCACTGGCTCTCCAAGTGCCAGAGGTGGGCAGGTGGTGGCAC
       TGAGCCCCCCCAACACTGTGCCCTGGTGGAGAAAGCACTGACCTGTCATGCCCCCCTCAA
       ACCTCCTCTTCTGACGTGCCTTTTGCACCCCTCCCATTAGGACAATCAGTCCCCTCCCAT
       CTGGGAGTCCCCTTTTCTTTTCTACCCTAGCCATTCCTGGTACCCAGCCATCTGCCCAGG
       GGTGCCCCCTCCTCTCCCATCCCCCTGCCCTCGTGGCCAGCCCGGCTGGTTTTGTAAGAT
       [A,G]
       CTGGGTTGGTGCACAGTGATTTTTTTTCTTGTAATTTAAACAGGCCCAGCATTGCTGGTTC
       TATTTAATGGACATGAGATAATGTTAGAGGTTTTAAAGTGATTAAACGTGCAGACTATGC
       AAACCAGGCCCAGTCTCCAGTGTGGTACCGTTGCTCCTGCATCGCAGCTGAGGATAGGGG
       GCCAGTTAGGCCTACACAGTGGCCTGCCTGCCTGGATGTGGGCCCAAGTCAGAAGGCCAA
       AGTCCTCCAAGGGGCGGGAGGATGCGCCAGCCCCTAGTGGAGGAGCTGGTGCCCCTGGGG

2159   TGCGGCCCAGCGCGGAGCAGGGGGGCTGGCAGGCGTCGGGACGGTCGGGCCGGTCCCGCC
       CGCCCCTTCCCCTCCACAGGCCCGCCCCGGGGCCTGGGCCAACTGAAACCGCGGGAGGAG
       GAAGCGCGGAATCAGGAACTGGCCGGGGTCCGCACCGGGCCTGAGTCGGTCCGAGGCCGT
       CCCAGGAGCAGCTGCCCGTGCGGGTACCTCTAGCCCCGGGGCCTGGAGGAGCGGTGGGAG
       CTGGGGGCGCGGCAGGCAGGGGCAGAGCAGGCGTTCCGAGGGCCAGAGACCCACCCAGGT
       [G,C]
       GGGGTAGGGGCCGCGGAAGGGCGGGGATGGCCGCAGGGGCAGGGCTCAGGCTGTGGGCGC
       CTGAGGCTTCAGCTGGGGCAGGCTTGGCCTGTCGAGGACCTGGGCAAGGGTGTCCCTGTA
       AGGGGTGGTGGGTGGAAGGGCCTGGGGAGGGAGGCTCCAGGTTGGCTCCTGTTCCCGAAC
       GTGCGGAGGAGACCCTGACGCTAAGGAAGCAATGAGGGCCAGTCCCCAGGCCAGGCTGCT
       GCTGGGTACCCATGGCTGCGTGTGAGCGAGGCAGGACCCCACCTCCTCCCCGTCTGCAGT

2484   GGATGGCCGCAGGGGCAGGGCTCAGGCTGTGGGCGCCTGAGGCTTCAGCTGGGGCAGGCT
       TGGCCTGTCGAGGACCTGGGCAAGGGTGTCCCTGTAAGGGGTGGTGGGTGGAAGGGCCTG
       GGGAGGGAGGCTCCAGGTTGGCTCCTGTTCCCGAACGTGCGGAGGAGACCCTGACGCTAA
       GGAAGCAATGAGGGCCAGTCCCCAGGCCAGGCTGCTGCTGGGTACCCATGGCTGCGTGTG
       AGCGAGGCAGGACCCCACCTCCTCCCCGTCTGCAGTCCATCCTGACCCTACAGTCCCCAG
       [C,T]
       CTCCTCGTCCCATGCCTCCGTCTCCAGCTGCTGCCTTGCCTCCAGGGATGGCCCCTTTTC
       TGTCCCCAGAACAGCACTATGGGCTTCTCTTCTGAGCTGTGCAGCCCCCAGGGCCACGGG
       GTCCTGCAGCAAATGCAGGAGGCCGAGCTTCGTCTACTGGAGGGCATGAGAAAGTGGATG
       GCCCAGCGGGTCAAGAGTGACAGGGAGTATGCAGGACTGCTTCACCACATGTCCCTGCAG
       GACAGTGGGGCCAGAGCCGGGCCATCAGCCCTGACAGCCCCATCAGTCAGGTGGGTCTC

2577   GTAAGGGGTGGTGGGTGGAAGGGCCTGGGGAGGGAGGCTCCAGGTTGGCTCCTGTTCCCG
       AACGTGCGGAGGAGACCCTGACGCTAAGGAAGCAATGAGGGCCAGTCCCCAGGCCAGGCT
       GCTGCTGGGTACCCATGGCTGCGTGTGAGCGAGGCAGGACCCCACCTCCTCCCCGTCTGC
       AGTCCATCCTGACCCTACAGTCCCCAGCCTCCTCGTCCCATGCCTCCGTCTCCAGCTGCT
       GCCTTGCCTCCAGGGATGGCCCCTTTTCTGTCCCCAGAACAGCACTATGGGCTTCTCTTC
```

FIG. 31

```
        [T,C]
        GAGCTGTGCAGCCCCCAGGGCCACGGGGTCCTGCAGCAAATGCAGGAGGCCGAGCTTCGT
        CTACTGGAGGGCATGAGAAAGTGGATGGCCCAGCGGGTCAAGAGTGACAGGGAGTATGCA
        GGACTGCTTCACCACATGTCCCTGCAGGACAGTGGGGGCCAGAGCCGGGCCATCAGCCCT
        GACAGCCCCATCAGTCAGGTGGGTCTCTATGGGACTCTGGTGGGTGCTGGCGTATCTGCC
        TTCTCCTTCCTCTCCTGGGGCCCTCTGGGGCAGTGGCTGGAGATCTGGCAGGCCAATGC

2808    CCAGCTGCTGCCTTGCCTCCAGGGATGGCCCCTTTTCTGTCCCCAGAACAGCACTATGGG
        CTTCTCTTCTGAGCTGTGCAGCCCCCAGGGCCACGGGGTCCTGCAGCAAATGCAGGAGGC
        CGAGCTTCGTCTACTGGAGGGCATGAGAAAGTGGATGGCCCAGCGGGTCAAGAGTGACAG
        GGAGTATGCAGGACTGCTTCACCACATGTCCCTGCAGGACAGTGGGGGCCAGAGCCGGGC
        CATCAGCCCTGACAGCCCCATCAGTCAGGTGGGTCTCTATGGGACTCTGGTGGGTGCTGG
        [-,T,C]
        GTATCTGCCTTCTCCTTCCTCTCCTGGGGCCCTCTGGGGCAGTGGCTGGAGATCTGGCA
        GGCCAATGCTTGGGAGCCATTGTGCCCCCCTCCCTGCCTCCCCCATCTGTGCTGTATAGT
        CCTGGGCTGAGATCACCAGCCAAACTGAGGGCCTGAGCCGCTTGCTGCGGCAGCACGCAG
        AGGATCTGAACTCAGGGCCCCTGAGCAAGCTGAGCCTGCTCATCCGGGAACGGCAGCAGC
        TTCGCAAGACCTACAGCGAGCAGTGGCAGCAGCTGCAGCAGGAGCTCACCAAGGTGAGCG

2922    GGAGGCCGAGCTTCGTCTACTGGAGGGCATGAGAAAGTGGATGGCCCAGCGGGTCAAGAG
        TGACAGGGAGTATGCAGGACTGCTTCACCACATGTCCCTGCAGGACAGTGGGGGCCAGAG
        CCGGGCCATCAGCCCTGACAGCCCCATCAGTCAGGTGGGTCTCTATGGGACTCTGGTGGG
        TGCTGGCGTATCTGCCTTCTCCTTCCTCTCCTGGGGCCCTCTGGGGCAGTGGCTGGAGA
        TCTGGCAGGCCAATGCTTGGGAGCCATTGTGCCCCCCTCCCTGCCTCCCCCATCTGTGCT
        [G,A]
        TATAGTCCTGGGCTGAGATCACCAGCCAAACTGAGGGCCTGAGCCGCTTGCTGCGGCAGC
        ACGCAGAGGATCTGAACTCAGGGCCCCTGAGCAAGCTGAGCCTGCTCATCCGGGAACGGC
        AGCAGCTTCGCAAGACCTACAGCGAGCAGTGGCAGCAGCTGCAGCAGGAGCTCACCAAGG
        TGAGCGGGCAGCACTGGGGCTTCGGTCATTTCTGTCTAAATTTTGAGCCTCGAAGGGGTT
        GTTTTGCACAAGAGGCCCTGGATTCACTGGGGAAGTGTAAGTCCCTGACCGCAGGCCTGG

4312    GGACGAGAACACTGATCTCGGGCTGTCATCTATTCCTACTGCCAAGAACATAATTTGCAG
        GACCCAGTGCAAAGTGAAATTGTGGGGGTCTTTGTTAAAAGATTGCTAGGAATTTCCAGG
        TGGCAATAATGGAGAATGAAACCAAGCACAGGGCCCTTCTACATGTGGAGCCCCGTGTGA
        CTGCACAGGCCGTGCACACCTGCAACTGGCCCTGCCTGCCACCAGGCTACCACTGTCAGT
        CCAAGGAGGGACCGTTGTAGCCTGTAGTCTACCTCTTTGCCTCCCCAAGGGGTCTGTCTT
        [C,T]
        AACAGGCTCTCTGATCTTTGACTCTCACGTCAGCAGCCAGCTTTCCCAGAAGTCTCCAGG
        TGCTCCTTGCCTGACGACAGGACCTTTCCAGGGCTTCACCCCAGGCAAGAATCTTCCACA
        ACTGGGGACCTGCTGCCCCACACTGGCCTCTCCTCTCTCCCTAGACCCACAGCCAGGACA
        TTGAGAAGCTGAAGAGCCAGTACCGAGCTCTGGCACGGGACAGTGCCCAAGCCAAGCGCA
        AGTACCAGGAGGCCAGCAAAGGTTCGTGGCTTCCCTTGCTGGCAGGGAGGGAATCCGAAG

4903    GAATCCGAAGCCAGTGCTGACCTGTCCTTGGGTACCCAGAGAGTGGGGGCTGCCTGGGCC
        TCCATGCTGTCATCTATACCCCTTGCCCCCCTTCTGGCAGACAAGGACCGTGACAAGGCC
        AAGGACAAGTATGTGCGCAGCCTGTGGAAGCTCTTTGCTCACCACAACCGCTATGTGCTG
```

FIG. 3J

```
         GGCGTGCGGGCTGCGCAGCTACACCACCAGCACCACCACCAGCTCCTGCTGCCCGGCCTG
         CTGCGGTCACTGCAGGACCTGCACGAGGAGATGGCTTGCATCCTGTAAGCCCGCAGCCCC
         [G,A]
         TCCCCTGGCCCCCACCCTTGAGCAGCCCTAAGCCCAGCCATCAGGCCCAGAGGCAGGACC
         CAGAAAATCCATTGCTGGGAAGGTGCTGGCCATGTAACCACATGAGAACGGGACCTGGGC
         CAAGGATTGGAAACAGGCAACTTACCTCTGAATTACACTATTCCAGGGTCTCATTATTCC
         AGGGTTTTATTACATTCATTGAGCACTGTTCTGGGCTCTGGATTATACCAGAGAACGATG
         GTAGACAAAAACATCTGTCCTCAGGGATCTTTCGTGTTAGTGGAGTGAGAATGTGAGGAG

5193     CCGCAGCCCCGTCCCCTGGCCCCCACCCTTGAGCAGCCCTAAGCCCAGCCATCAGGCCCA
         GAGGCAGGACCCAGAAAATCCATTGCTGGGAAGGTGCTGGCCATGTAACCACATGAGAAC
         GGGACCTGGGCCAAGGATTGGAAACAGGCAACTTACCTCTGAATTACACTATTCCAGGGT
         CTCATTATTCCAGGGTTTTATTACATTCATTGAGCACTGTTCTGGGCTCTGGATTATACC
         AGAGAACGATGGTAGACAAAAACATCTGTCCTCAGGGATCTTTCGTGTTAGTGGAGTGAG
         [A,G]
         ATGTGAGGAGCACTAAGAGCCATGGAGAAAAATAAAGCAAGAGAAGTGGATCGGGACCTG
         GGAGCACGGAGGCAAGGGAGGAGGTGACAGTTGTCCATAGAGTGATCTGGGAAAGCCTCT
         TGAGAGGTGACATTCAAAGAGGCCCCTGAGAGGGGTACGGGAGTGAATCATGGGGCTATT
         TGGAGAAAGACCATTCCAGAAAGGAGGACAGCAATTACACAGGCCTTGAGGTAGGAGAGT
         ACCAGGGACTAATAGCCAGGAACCAGTGGTGCCTCTGAGAGTGAGGGAGGGGGAGAGTCA
```

FIG. 3K

US 6,340,584 B1

ISOLATED HUMAN KINASE PROTEINS, NUCLEIC ACID MOLECULES ENCODING HUMAN KINASE PROTEINS, AND USES THEREOF

FIELD OF THE INVENTION

The present invention is in the field of kinase proteins that are related to the proto-oncogene tyrosine kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast.

The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Proto-oncogene Tyrosine Kinases

The novel human protein, and encoding gene, provided by the present invention is related to proto-oncogene tyrosine kinases such as v-fes/fps and c-fes/fps. The protein of the present invention shows the highest degree of similarity to the protein provided in Genbank gi4503687 (see the amino acid sequence alignment provided in FIG. 2), "V-FES feline sarcoma viral/V-FPS fujinami avian sarcoma viral oncogene homolog", also referred to as "V-FES/FPS", "oncogene FES", "feline sarcoma virus", and "FPS". The art-known V-FES/FPS protein of gi4503687 is a human cellular homolog of a feline sarcoma retrovirus protein that has transforming properties, tyrosine-specific protein kinase activity, and activity necessary for maintenance of cellular transformation. Furthermore, V-FES/FPS is involved in hematopoiesis and is associated with a chromosomal translocation event found in patients with acute promyelocytic leukemia.

For a further review of proto-oncogene tyrosine kinases, see Roebroek et al., *EMBO J.* 4 (11), 2897–2903 (1985); Roebroek et al., *Mol. Biol. Rep.* 11 (2), 117–125 (1986); Alcalay et al., *Oncogene* 5 (3), 267–275 (1990); Polymeropoulos et al., *Nucleic Acids Res.* 19 (14), 4018 (1991); Bowden et al., *Nucleic Acids Res.* 19 (15), 4311 (1991); Jucker et al., *Oncogene* 7 (5), 943–952 (1992); Mathew et al., *Cytogenet. Cell Genet.* 63 (1), 33–34 (1993); and Smithgall et al., *Crit Rev Oncog* 9 (1), 43–62 (1998).

Kinase proteins, particularly members of the proto-oncogene tyrosine kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the proto-oncogene tyrosine kinase subfamily.

SUMMARY OF THE INVENTION

The present invention is based in part on the identification of amino acid sequences of human kinase peptides and proteins that are related to the proto-oncogene tyrosine kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in placenta, lung tumors, kidney tumors, pregnant uterus, leukemia, stomach adenocarcinoma, and hippocampus.

DESCRIPTION OF THE FIGURE SHEETS

FIG. 1 provides the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in placenta, lung tumors, kidney tumors, pregnant uterus, leukemia, stomach adenocarcinoma, and hippocampus.

FIG. 2 provides the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 10 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the proto-oncogene tyrosine kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the proto-oncogene tyrosine kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the proto-oncogene tyrosine kinase subfamily and the expression pattern observed. Experimental data as provided in FIG. 1 indicates expression in humans in placenta, lung tumors, kidney tumors, pregnant uterus, leukemia, stomach adenocarcinoma, and hippocampus. The art has clearly established the commercial importance of members of this family of proteins and proteins that have, expression patterns similar to that of the present gene. Some of the more specific features of the peptides of the present invention, and the uses thereof, are described herein, particularly in the Background of the Invention and in the annotation provided in the Figures, and/or are known within the art for each of the known proto-oncogene tyrosine kinase family or subfamily of kinase proteins.

Specific Embodiments

Peptide Molecules

The present invention provides nucleic acid sequences that encode protein molecules that have been identified as being members of the kinase family of proteins and are related to the proto-oncogene tyrosine kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in placenta, lung tumors, kidney tumors, pregnant uterus, leukemia, stomach adenocarcinoma, and hippocampus. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol.*

*Biol.* 215:403–10 (1990)). BLAST nucleotide searches can be performed with the NBLAST program, score =100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 15 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 15 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 10 different nucleotide positions. Some of these SNPs that are located outside the ORF and in introns may affect gene transcription.

Paralogs of a kinase peptide can readily be identified as having some degree of significant sequence homology/ identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/ identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile, interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/ regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, ganmma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that the kinase proteins of the present invention are expressed in humans in the placenta, lung tumors, kidney tumors, pregnant uterus, leukemia, and stomach adenocarcinoma as indicated by virtual northern blot analysis. In addition, PCR-based tissue screening panels indicate expression in the hippocampus. A large percentage of pharmaceutical agents are being developed that modulate the activity of kinase proteins, particularly members of the proto-oncogene tyrosine kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in placenta, lung tumors, kidney tumors, pregnant uterus, leukemia, stomach adenocarcinoma, and hippocampus. Such uses can readily be determined using the information provided herein, that which is known in the art, and routine experimentation.

The proteins of the present invention (including variants and fragments that may have been disclosed prior to the present invention) are useful for biological assays related to kinases that are related to members of the proto-oncogene tyrosine kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that the kinase proteins of the present invention are expressed in humans in the placenta, lung tumors, kidney tumors, pregnant uterus, leukemia, and stomach adenocarcinoma as indicated by virtual northern blot analysis. In addition, PCR-based tissue screening panels indicate expression in the hippocampus.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in placenta, lung tumors, kidney tumors, pregnant uterus, leukemia, stomach adenocarcinoma, and hippocampus. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that the kinase proteins of the present invention are expressed in humans in the placenta, lung tumors, kidney tumors, pregnant uterus, leukemia, and stomach adenocarcinoma as indicated by virtual northern blot analysis. In addition, PCR-based tissue screening panels indicate expression in the hippocampus.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in placenta, lung tumors, kidney tumors, pregnant uterus, leukemia, stomach adenocarcinoma, and hippocampus. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in placenta, lung tumors, kidney tumors, pregnant uterus, leukemia, stomach adenocarcinoma, and hippocampus. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in placenta, lung tumors, kidney tumors, pregnant uterus, leukemia, stomach adenocarcinoma, and hippocampus. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the kinase proteins of the present invention are expressed in humans in the placenta, lung tumors, kidney tumors, pregnant uterus, leukemia, and stomach adenocarcinoma as indicated by virtual northern blot analysis. In addition, PCR-based tissue screening panels indicate expression in the hippocampus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in placenta, lung tumors, kidney tumors, pregnant uterus, leukemia, stomach adenocarcinoma, and hippocampus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in placenta, lung tumors, kidney tumors, pregnant uterus, leukemia, stomach adenocarcinoma, and hippocampus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in placenta, lung tumors, kidney tumors, pregnant uterus, leukemia, stomach adenocarcinoma, and hippocampus. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 15 (as indicated in FIG. 3), which is supported by multiple lines of evidence, such as STS and BAC map data.

FIG. 3 provides information on SNPs that have been found in the gene encoding the kinase protein of the present invention. SNPs were identified at 10 different nucleotide positions. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2× SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 10 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 15 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the kinase proteins of the present invention are expressed in humans in the placenta, lung tumors, kidney tumors, pregnant uterus, leukemia, and stomach adenocarcinoma as indicated by virtual northern blot analysis. In addition, PCR-based tissue screening panels indicate expression in the hippocampus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that the kinase proteins of the present invention are expressed in humans in the placenta, lung tumors, kidney tumors, pregnant uterus, leukemia, and stomach adenocarcinoma as indicated by virtual northern blot analysis. In addition, PCR-based tissue screening panels indicate expression in the hippocampus.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in placenta, lung tumors, kidney tumors, pregnant uterus, leukemia, stomach adenocarcinoma, and hippocampus. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that the kinase proteins of the present invention are expressed in humans in the placenta, lung tumors, kidney tumors, pregnant uterus, leukemia, and stomach adenocarcinoma as indicated by virtual northern blot analysis. In addition, PCR-based tissue screening panels indicate expression in the hippocampus. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in placenta, lung tumors, kidney tumors, pregnant uterus, leukemia, stomach adenocarcinoma, and hippocampus.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 10 different nucleotide positions. Some of these SNPs that are located outside the ORF and in introns may affect gene transcription. The gene encoding the novel kinase protein of the present invention is located on a genome component that has been mapped to human chromosome 15 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 10 different nucleotide positions. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that the kinase proteins of the present invention are expressed in humans in the placenta, lung tumors, kidney tumors, pregnant uterus, leukemia, and stomach adenocarcinoma as indicated by virtual northern blot analysis. In addition, PCR-based tissue screening panels indicate expression in the hippocampus. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS: 1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14:1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 10 different nucleotide positions. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccina viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933– 943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed, Cold Spring Harbor Laboratory Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell- free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. An isolated nucleic acid molecule consisting of a nucleotide sequence selected from the group consisting of:
   (a) a nucleotide sequence that encodes an amino acid sequence shown in SEQ ID NO:2;
   (b) a nucleic acid molecule consisting of the nucleic acid sequence of SEQ ID NO:1;
   (c) a nucleic acid molecule consisting of the nucleic acid sequence of SEQ ID NO:3; and
   (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

* * * * *

SEQUENCE LISTING

```
<160> NUMBER OF SEQ ID NOS: 4

<210> SEQ ID NO 1
<211> LENGTH: 2674
<212> TYPE: DNA
<213> ORGANISM: Human

<400> SEQUENCE: 1 tccgggtcc  gcaccgggcc  tgagtcggtc  cgaggccgtc  ccaggagcag  ctgcccgtgc     60
ggaacagcac  tatgggcttc  tcttctgagc  tgtgcagccc  ccagggccac  ggggtcctgc    120
agcaaatgca  ggaggccgag  cttcgtctac  tggagggcat  gagaaagtgg  atggcccagc    180
gggtcaagag  tgacagggag  tatgcaggac  tgcttcacca  catgtccctg  caggacagtg    240
ggggccagag  ccgggccatc  agccctgaca  gccccatcag  tcagtcctgg  gctgagatca    300
```

-continued

| | | |
|---|---|---|
| ccagccaaac tgagggcctg agccgcttgc tgcggcagca cgcagaggat ctgaactcag | 360 |
| ggcccctgag caagctgagc ctgctcatcc gggaacggca gcagcttcgc aagacctaca | 420 |
| gcgagcagtg gcagcagctg cagcaggagc tcaccaagac ccacagccag gacattgaga | 480 |
| agctgaagag ccagtaccga gctctggcac gggacagtgc ccaagccaag cgcaagtacc | 540 |
| aggaggccag caaagacaag gaccgtgaca aggccaagga caagtatgtg cgcagcctgt | 600 |
| ggaagctctt tgctcaccac aaccgctatg tgctgggcgt gcgggctgcg cagctacacc | 660 |
| accagcacca ccaccagctc ctgctgcccg gcctgctgcg gtcactgcag gacctgcacg | 720 |
| aggagatggc ttgcatcctg aaggagatcc tgcaggaata cctggagatt gcagcctgg | 780 |
| tgcaggatga ggtggtggcc attcaccggg agatggctgc agctgctgcc cgcatccagc | 840 |
| ctgaggctga gtaccaaggc ttcctgcgac agtatgggtc cgcacctgac gtcccaccct | 900 |
| gtgtcacgtt cgatgagtca ctgcttgagg agggtgaacc gctggagcct ggggagctcc | 960 |
| agctgaacga gctgactgtg gagagcgtgc agcacacgct gacctcagtg acagatgagc | 1020 |
| tggctgtggc caccgagatg gtgttcaggc ggcaggagat ggttacgcag ctgcaacagg | 1080 |
| agctccggaa tgaagaggag aacacccacc cccgggagcg ggtgcagctg ctgggcaaga | 1140 |
| ggcaagtgct gcaagaagca ctgcaggggc tgcaggtagc gctgtgcagc caggccaagc | 1200 |
| tgcaggccca gcaggagttg ctgcagacca agctggcagc cctgggcccc ggcgagcccc | 1260 |
| cgcctgtgct gctcctgcag gatgaccgcc actccacgtc gtcctcggag caggagcgag | 1320 |
| aggggggaag gacacccacg ctggagatcc ttaagagcca catctcagga atcttccgcc | 1380 |
| ccaagttctc gaacctgtac cgactggaag gggaaggctt tcctagcatt cctttgctca | 1440 |
| tcgaccacct actgagcacc cagcagcccc tcaccaagag gagtggtgtt gtcctgcaca | 1500 |
| gggctgtgcc caaggacaag tgggtgctga accatgagga cctggtgttg ggtgagcaga | 1560 |
| ttggacgggg gaactttggc gaagtgttca gcggacgcct gcgagccgac aacacccctgg | 1620 |
| tggcggtgaa gtcttgtcga gagacgctcc cacctgacct caaggccaag tttctacagg | 1680 |
| aagcgaggat cctgaagcag tacagccacc ccaacatcgt gcgtctcatt ggtgtctgca | 1740 |
| cccagaagca gcccatctac atcgtcatgg agcttgtgca gggggggcgac ttcctgacct | 1800 |
| tcctccgcac ggagggggcc cgcctgcggg tgaagactct gctgcagatg gtgggggatg | 1860 |
| cagctgctgg catggagtac ctggagagca agtgctgcat ccaccgggac ctggctgctc | 1920 |
| ggaactgcct ggtgacagag aagaatgtcc tgaagatcag tgactttggg atgtcccgag | 1980 |
| aggaagccga tgggtctat gcagcctcag ggggcctcag acaagtcccc gtgaagtgga | 2040 |
| ccgcacctga ggcccttaac tacggccgct actcctccga aagcgacgtg tggagctttg | 2100 |
| gcatcttgct ctgggagacc ttcagcctgg gggcctcccc ctatcccaac ctcagcaatc | 2160 |
| agcagacacg ggagtttgtg gagaaggggg gccgtctgcc ctgccagag ctgtgtcctg | 2220 |
| atgccgtgtt caggctcatg gagcagtgct gggcctatga gcctgggcag cggcccagct | 2280 |
| tcagcaccat ctaccaggag ctgcagagca tccgaaagcg catcggtga ggctgggacc | 2340 |
| cccttctcaa gctggtggcc tctgcaggcc taggtgcagc tcctcagcgg ctccagctca | 2400 |
| tatgctgaca gctcttcaca gtcctggact cctgccacca gcatccacac tgccggcagg | 2460 |
| atgcagcgcc gtgtcctctc tgtgtccctg ctgctgccag ggcttcctct tccgggcaga | 2520 |
| aacaataaaa ccacttgtgc ccactgaaaa aaaaaaaaaa aaaaaaaaaa aaaaaaaaaa | 2580 |
| aaaaaaaaaa aaaaaaaaaa aaaaaaaaaa aaaaaaaaaa aaaaaaaaaa aaaaaaaaaa | 2640 |
| aaaaaaaaaa aaaaaaaaaa aaaaaaaaaa aaaa | 2674 |

```
<210> SEQ ID NO 2
<211> LENGTH: 752
<212> TYPE: PRT
<213> ORGANISM: Human

<400> SEQUENCE: 2

Met Gly Phe Ser Ser Glu Leu Cys Ser Pro Gln Gly His Gly Val Leu
 1               5                  10                  15

Gln Gln Met Gln Glu Ala Glu Leu Arg Leu Leu Glu Gly Met Arg Lys
                20                  25                  30

Trp Met Ala Gln Arg Val Lys Ser Asp Arg Glu Tyr Ala Gly Leu Leu
            35                  40                  45

His His Met Ser Leu Gln Asp Ser Gly Gly Gln Ser Arg Ala Ile Ser
        50                  55                  60

Pro Asp Ser Pro Ile Ser Gln Ser Trp Ala Glu Ile Thr Ser Gln Thr
65                  70                  75                  80

Glu Gly Leu Ser Arg Leu Leu Arg Gln His Ala Glu Asp Leu Asn Ser
                85                  90                  95

Gly Pro Leu Ser Lys Leu Ser Leu Leu Ile Arg Glu Arg Gln Gln Leu
            100                 105                 110

Arg Lys Thr Tyr Ser Glu Gln Trp Gln Gln Leu Gln Gln Glu Leu Thr
        115                 120                 125

Lys Thr His Ser Gln Asp Ile Glu Lys Leu Lys Ser Gln Tyr Arg Ala
    130                 135                 140

Leu Ala Arg Asp Ser Ala Gln Ala Lys Arg Lys Tyr Gln Glu Ala Ser
145                 150                 155                 160

Lys Asp Lys Asp Arg Asp Lys Ala Lys Asp Lys Tyr Val Arg Ser Leu
                165                 170                 175

Trp Lys Leu Phe Ala His His Asn Arg Tyr Val Leu Gly Val Arg Ala
            180                 185                 190

Ala Gln Leu His His Gln His His Gln Leu Leu Leu Pro Gly Leu
        195                 200                 205

Leu Arg Ser Leu Gln Asp Leu His Glu Glu Met Ala Cys Ile Leu Lys
    210                 215                 220

Glu Ile Leu Gln Glu Tyr Leu Glu Ile Ser Ser Leu Val Gln Asp Glu
225                 230                 235                 240

Val Val Ala Ile His Arg Glu Met Ala Ala Ala Ala Arg Ile Gln
                245                 250                 255

Pro Glu Ala Glu Tyr Gln Gly Phe Leu Arg Gln Tyr Gly Ser Ala Pro
            260                 265                 270

Asp Val Pro Pro Cys Val Thr Phe Asp Glu Ser Leu Leu Glu Glu Gly
        275                 280                 285

Glu Pro Leu Glu Pro Gly Glu Leu Gln Leu Asn Glu Leu Thr Val Glu
    290                 295                 300

Ser Val Gln His Thr Leu Thr Ser Val Thr Asp Glu Leu Ala Val Ala
305                 310                 315                 320

Thr Glu Met Val Phe Arg Arg Gln Glu Met Val Thr Gln Leu Gln Gln
                325                 330                 335

Glu Leu Arg Asn Glu Glu Asn Thr His Pro Arg Glu Arg Val Gln
            340                 345                 350

Leu Leu Gly Lys Arg Gln Val Leu Gln Glu Ala Leu Gln Gly Leu Gln
        355                 360                 365

Val Ala Leu Cys Ser Gln Ala Lys Leu Gln Ala Gln Gln Glu Leu Leu
```

-continued

```
                        370                 375                 380
Gln Thr Lys Leu Glu His Leu Gly Pro Gly Glu Pro Pro Val Leu
385                 390                 395                 400
Leu Leu Gln Asp Asp Arg His Ser Thr Ser Ser Glu Gln Glu Arg
                405                 410                 415
Glu Gly Gly Arg Thr Pro Thr Leu Glu Ile Leu Lys Ser His Ile Ser
            420                 425                 430
Gly Ile Phe Arg Pro Lys Phe Ser Asn Leu Tyr Arg Leu Glu Gly Glu
                435                 440                 445
Gly Phe Pro Ser Ile Pro Leu Leu Ile Asp His Leu Leu Ser Thr Gln
            450                 455                 460
Gln Pro Leu Thr Lys Lys Ser Gly Val Val Leu His Arg Ala Val Pro
465                 470                 475                 480
Lys Asp Lys Trp Val Leu Asn His Glu Asp Leu Val Leu Gly Glu Gln
                485                 490                 495
Ile Gly Arg Gly Asn Phe Gly Glu Val Phe Ser Gly Arg Leu Arg Ala
                500                 505                 510
Asp Asn Thr Leu Val Ala Val Lys Ser Cys Arg Glu Thr Leu Pro Pro
            515                 520                 525
Asp Leu Lys Ala Lys Phe Leu Gln Glu Ala Arg Ile Leu Lys Gln Tyr
            530                 535                 540
Ser His Pro Asn Ile Val Arg Leu Ile Gly Val Cys Thr Gln Lys Gln
545                 550                 555                 560
Pro Ile Tyr Ile Val Met Glu Leu Val Gln Gly Gly Asp Phe Leu Thr
                565                 570                 575
Phe Leu Arg Thr Glu Gly Ala Arg Leu Arg Val Lys Thr Leu Leu Gln
                580                 585                 590
Met Val Gly Asp Ala Ala Ala Gly Met Glu Tyr Leu Glu Ser Lys Cys
                595                 600                 605
Cys Ile His Arg Asp Leu Ala Ala Arg Asn Cys Leu Val Thr Glu Lys
                610                 615                 620
Asn Val Leu Lys Ile Ser Asp Phe Gly Met Ser Arg Glu Glu Ala Asp
625                 630                 635                 640
Gly Val Tyr Ala Ala Ser Gly Gly Leu Arg Gln Val Pro Val Lys Trp
                645                 650                 655
Thr Ala Pro Glu Ala Leu Asn Tyr Gly Arg Tyr Ser Ser Glu Ser Asp
                660                 665                 670
Val Trp Ser Phe Gly Ile Leu Leu Trp Glu Thr Phe Ser Leu Gly Ala
                675                 680                 685
Ser Pro Tyr Pro Asn Leu Ser Asn Gln Gln Thr Arg Glu Phe Val Glu
                690                 695                 700
Lys Gly Gly Arg Leu Pro Cys Pro Glu Leu Cys Pro Asp Ala Val Phe
705                 710                 715                 720
Arg Leu Met Glu Gln Cys Trp Ala Tyr Glu Pro Gly Gln Arg Pro Ser
                725                 730                 735
Phe Ser Thr Ile Tyr Gln Glu Leu Gln Ser Ile Arg Lys Arg His Arg
                740                 745                 750

<210> SEQ ID NO 3
<211> LENGTH: 15297
<212> TYPE: DNA
<213> ORGANISM: Human

<400> SEQUENCE: 3
```

-continued

```
ctggccacca ggctggcgca gccaaggccg aagctctggc tgaaccctgt gctggtgtcc      60
tgaccaccct ccctctcttt gcacccgcct ctcccgtcag ggcccaagtc cctgttttct     120
gagcccgggc tgcctgggct gttggcactc acagacctgg agccctgggt gggtggtgg     180
ggagggggcgc tggcccagcc ggcctctctg gcctccacc cgatgctgct tccccctgtg     240
gggatctcag gggctgtttg aggatatatt ttcactttgt gattatttca ctttagatgc     300
tgatgatttg ttttgtatt tttaatgggg gtagcagctg gactacccac gttctcacac      360
ccaccgtccg ccctgctcct ccctggctgc cctggccctg aggtgtgggg gctgcagcat     420
gttgctgagg agtgaggaat agttgagccc caagtcctga gaggcgggc cagccaggcg      480
ggctcaagga aaggggtcc cagtgggagg ggcaggctga catctgtgtt tcaagtgggg     540
ctcgccatgc cgggggttca taggtcactg gctctccaag tgccagaggt gggcaggtgg     600
tggcactgag cccccccaac actgtgccct ggtggagaaa gcactgacct gtcatgcccc     660
cctcaaacct cctcttctga cgtgcctttt gcacccctcc cattaggaca atcagtcccc     720
tcccatctgg gagtccccctt ttcttttcta ccctagccat tcctggtacc cagccatctg   780
cccagggggtg ccccctcctc tcccatcccc ctgccctcgt ggccagcccg gctggttttg    840
taagatactg ggttggtgca cagtgatttt tttcttgtaa tttaaacagg cccagcattg    900
ctggttctat ttaatggaca tgagataatg ttagaggttt taaagtgatt aaacgtgcag    960
actatgcaaa ccaggcccag tctccagtgt ggtaccgttg ctcctgcatc gcagctgagg    1020
ataggggggcc agttaggcct acacagtggc ctgcctgcct ggatgtgggc caagtcaga    1080
aggccaaagt cctccaaggg gcgggaggat gcgccagccc ctagtggagg agctggtgcc   1140
cctggggtgg ggctggtgac ccctggtcct caggagctga gcactaaact cccaaagtcc   1200
tggtttccag cagtgtgaag aactgggcct attgtgtctt cctgggctga agtgatctgg   1260
tcgccacagg ctatagggct gaggcctaag gtggagggag gcctgactga atcaagatga   1320
cttcttgtgg ggagcctgag tcccaaatgg aaaactccac gcctgtccgc tccccaaccc    1380
ctgccccttg atttccccag gtctccccttg ggacaggaag cccctgcctg ggggtaggag   1440
gatgggggaca aaaccactag gatctgtatc cgagaagcag tctctgttcg ggatatttac   1500
ttggaaattt tattcaaatg gaagctggcg cctgagcctc tccttaggga attccgtgag    1560
gtggggaggg ctgggaccag ggttccctct ttctcttctg cggtggccct ggcctggtgc    1620
taggactgcg cgcctcccct cagtacccgc ggacaccctg gcttccctg ggcccagcat     1680
ctgcctgggg cctcgccctg ggctcccct cctgaccccc accttgcgcc ccttcccggt    1740
gttcccgggg cgctgccggg ccctggggcc tgcggggcgc gggcggctct tggctgggcc   1800
attctttccc ggccccctcc tcccttccgt ttccgtggcc gtgcggccgg ctagaggctg   1860
cggcccagcg cggagcaggg gggctggcag gcgtcgggac ggtcgggccg gtcccgcccg   1920
ccccttcccc tccacaggcc cgccccgggg cctgggccaa ctgaaaccgc gggaggagga    1980
agcgcggaat caggaactgg ccgggggtccg caccgggcct gagtcggtcc gaggccgtcc   2040
caggagcagc tgcccgtgcg ggtacctcta gccccggggc ctggaggagc ggtgggagct    2100
gggggcgcgg caggcagggg cagagcaggc gttccgaggg ccagagaccc acccaggtgg   2160
gggtaggggc cgcggaaggg cggggatggc cgcagggca gggctcaggc tgtgggcgcc    2220
tgaggcttca gctggggcag gcttggcctg tcgaggacct gggcaagggt gtccctgtaa    2280
ggggtggtgg gtggaagggc ctggggaggg aggctccagg ttggctcctg ttcccgaacg    2340
tgcggaggag accctgacgc taaggaagca atgagggcca gtccccaggc caggctgctg   2400
```

-continued

```
ctgggtaccc atggctgcgt gtgagcgagg caggacccca cctcctcccc gtctgcagtc    2460
catcctgacc ctacagtccc cagcctcctc gtcccatgcc tccgtctcca gctgctgcct    2520
tgcctccagg gatggcccct tttctgtccc cagaacagca ctatgggctt ctcttctgag    2580
ctgtgcagcc cccagggcca cggggtcctg cagcaaatgc aggaggccga gcttcgtcta    2640
ctggagggca tgagaaagtg gatggcccag cgggtcaaga gtgacaggga gtatgcagga    2700
ctgcttcacc acatgtccct gcaggacagt gggggccaga gccgggccat cagccctgac    2760
agccccatca gtcaggtggg tctctatggg actctggtgg gtgctggcgt atctgccttc    2820
tccttcctct cctgggggcc ctctgggcca gtggctggag atctggcagg ccaatgcttg    2880
ggagccattg tgcccccctc cctgcctccc ccatctgtgc tgtatagtcc tgggctgaga    2940
tcaccagcca aactgagggc ctgagccgct tgctgcggca gcacgcagag gatctgaact    3000
cagggcccct gagcaagctg agcctgctca tccgggaacg gcagcagctt cgcaagacct    3060
acagcgagca gtggcagcag ctgcagcagg agctcaccaa ggtgagcggg cagcactggg    3120
gcttcggtca tttctgtcta aattttgagc ctcgaagggg ttgttttgca caagaggccc    3180
tggattcact ggggaagtgt aagtccctga ccgcaggcct ggcttgctct aaccttgatg    3240
tagcttcctc tcttccttcc cctacgttga gctggcttgc agcaaggcct ctctgtgctt    3300
tttctgtgcc tgggcaaagt gctgggagtg taaggatgag tgaccggtca cgtgcctggg    3360
agaagctcag aatcggtact cgcctccaca ctgtgccatc tggctctggg ttctgagagt    3420
cagggagagg aatgagggtc agtctgtttg ccttcgacct atgcagcctc ctctcagggc    3480
cccagagact gggcagcagc atggccccccc gaaggtcgag gactcgggcc gtgaagtcag    3540
cctgcctagg tttgaatccc acccagctcc tcagtctaga ggctgtgtga tttggaacta    3600
tttatctggg agcctagtgc ccccattcag tgtgctggtc accctccctg caccacaccc    3660
cttcctcaag tgcagagccc agccttgcca tggacccaca gcggcccctg gtggccaccc    3720
tggccccatt cctcgcccca aaagatcatc tgattcaagg gtgggcccat ttttataaag    3780
ttttgctgga acacagctat gccccttttgt tttcatattg tctgtgacta caatgacaga    3840
gttgagtaat tgtgacagag gctctatggc ctacaagcct aaaatattta tttactatct    3900 ggcccttttaa gaaaaagact gatctagtcg aggaatctag ctcagttaca gatggggaaa    3960
ctgaggttgg gcgcttgccc aacatatccc agcacataaa caggagaact gggacgagaa    4020
cactgatctc gggctgtcat ctattcctac tgccaagaac ataatttgca ggacccagtg    4080
caaagtgaaa ttgtgggggt cttttgttaaa agattgctag gaatttccag gtggcaataa    4140
tggagaatga aaccaagcac agggcccttc tacatgtgga gccccgtgtg actgcacagg    4200
ccgtgcacac ctgcaactgg ccctgcctgc caccaggcta ccactgtcag tccaaggagg    4260
gaccgttgta gcctgtagtc tacctctttg cctccccaag gggtctgtct tcaacaggct    4320
ctctgatctt tgactctcac gtcagcagcc agctttccca gaagtctcca ggtgctcctt    4380
gcctgacgac aggacctttc cagggcttca ccccaggcaa gaatcttcca caactgggga    4440
cctgctgccc cacactggcc tctcctctct ccctagaccc acagccagga cattgagaag    4500
ctgaagagcc agtaccgagc tctggcacgg gacagtgccc aagccaagcg caagtaccag    4560
gaggccagca aaggttcgtg gcttcccttg ctggcaggga gggaatccga agccagtgct    4620
gacctgtcct tgggtaccca gagagtgggg gctgcctggg cctccatgct gtcatctata    4680 cccccttgccc cccttctggc agacaaggac cgtgacaagg ccaaggacaa gtatgtgcgc    4740
```

```
agcctgtgga agctctttgc tcaccacaac cgctatgtgc tgggcgtgcg ggctgcgcag    4800
ctacaccacc agcaccacca ccagctcctg ctgcccggcc tgctgcggtc actgcaggac    4860
ctgcacgagg agatggcttg catcctgtaa gcccgcagcc ccgtcccctg gcccccaccc    4920
ttgagcagcc ctaagcccag ccatcaggcc cagaggcagg acccagaaaa tccattgctg    4980
ggaaggtgct ggccatgtaa ccacatgaga acgggacctg gccaaggat tggaaacagg     5040
caacttacct ctgaattaca ctattccagg gtctcattat tccagggttt tattacattc    5100
attgagcact gttctgggct ctggattata ccagagaacg atggtagaca aaaacatctg    5160
tcctcaggga tctttcgtgt tagtggagtg agaatgtgag gagcactaag agccatggag    5220
aaaaataaag caagagaagt ggatcgggac ctggggagcac ggaggcaagg gaggaggtga   5280
cagttgtcca tagagtgatc tgggaaagcc tcttgagagg tgacattcaa agaggcccct    5340
gagagggta cggagtgaa tcatgggct atttggagaa agaccattcc agaaaggagg       5400
acagcaatta cacaggcctt gaggtaggag agtaccaggg actaatagcc aggaaccagt    5460
ggtgcctctg agagtgaggg aggggagag tcatacacga ggctggagga ggcaggcgtc     5520
aagggctact gggtgataga aggtctagca gggccatggt gaggactttg gctctgggtg    5580
aacaagaatg gcatgatctg acctctgttt ttttgtttca ttttgtttta acttttttg     5640
agtcagagtc tcgctctgcc gcccaggcta gagtgcagtg gcatgatctc ggcttactgc    5700
aacctccgcc tcccaggttc aagtgattcc cctgcctcag cctccgagt agctgaaact     5760
acgggcatgc gccaccacac ccagctaatt tttgtatttt tagtagagac ggggtttcac    5820
catgttgccc aggctagtct ctaattcctg ggctcaaagc gatttgcctg cctctgcctc    5880
ccaaagtgcc gggattacag gcatgagcca ccatgcccag ccctgacctc tgttttaata   5940
aggccactct ggctgctgtg ctgcaaatag acttcaggga gcaaggacag aagctgggag    6000
gccagagagc aggctgcttg ccataatcca gatccaagct tttggccagc taggacgggg    6060
aggtagcaat ggaggtgagg cgcggtcagg tcctgggca ggtcctggaa ggtgaagcca     6120
gtgggatttc cctatggatt ggaagtgggg cgtgaaatag aggagtcagg ggtcactctg    6180
gggatttggc ctggagcagc tggaagatgg agtggctgtt aacttatgta gggaaggctg    6240
tgggaagaag aggtttagga gacaaggata gcagttcatt tatttattta tttatttatt    6300
tatttattta tttatttaga gatgtagtct cattctttcg ccaggctgga gtgcagtggc    6360
gcgatcttgg ctcactgcaa cctccacctc ccaggctcaa gcgattctct tgcctcagcc    6420
tcccgagtag ccaagtagct gggactacag gcatgtgcca ccatgcctgg ctaattttg    6480
tatttgcttt ttcagtagag atggggtttc accacgttag ccaggctggt ctcgaactga    6540
cctcaggcaa tccacccgcc tcgacctccc agtgttggta ttataggcgt gagccactgt    6600
gcctggccca ctgatccttt attacaactg ccagtgtccc tcttatatat atcaggaaat    6660
agaagattag ggagaggtta ataatttgc ctagagtggc atggctagct cgaagtgagg     6720
cagggtcaa cccagccct gactccaaac ccagggtcct aggcctgaac tgcccagcct      6780
tgcccagcct gaggctcccc tgactgggga tccgtctcg ggggcaggaa ggagatcctg     6840
caggaatacc tggagattag cagcctggtg caggatgagg tggtggccat tcaccgggag    6900
atggctgcag ctgctgcccg catccagcct gaggctgagt accaaggctt cctgcgacag    6960
tatgggtaag cccgtcctt gctcctgctg ggccagggc tgctggcctg tccactgacg      7020
gggcgctgtc ccccacaggt ccgcacctga cgtcccaccc tgtgtcacgt tcgatgagtc    7080
actgcttgag gagggtgaac cgctggagcc tggggagctc cagctgaacg agctgactgt    7140
```

-continued

```
ggagagcgtg cagcacacgt gggtggtggc tttgcacctg ggctgcggcg gggctcccag   7200
cagaccacga gtgtttatgt aggcagggct aggtcgtgga gactgtccac acagagctgt   7260
caccaggtgg ccgggcttgc ttggctctac agggatgcac tggacctggg ttgaggggc   7320 aggagggctc ggttctaatg ctgcccttct cttgggtgca ggctgacctc agtgacagat   7380
gagctggctg tggccaccga gatggtgttc aggcggcagg agatggttac gcagctgcaa   7440
caggagctcc ggaatgaaga ggagaacacc cacccccggg agcggtgagt gggcccctgc   7500
ctgcagcagc ctcctgggcc tccctccctc ctacctaccc taactgctgc tggctagccg   7560
ccgcagaccg agcccttatt cttcatccac cctcccaccc gccctgcct gcagggtgca   7620 gctgctgggc aagaggcaag tgctgcaaga agcactgcag gggctgcagg tagcgctgtg   7680
cagccaggcc aagctgcagg cccagcagga gttgctgcag accaagctgg agcacctggg   7740
ccccggcgag ccccgcctg tgctgctcct gcaggatgac cgccactcca cgtcgtcctc   7800
ggtgagctgc cccatccgcg gccgctgccc gccaccggcc tgcccacctg ggctgcgct   7860 cctcattttc gccctccccc tcctaagcc tggccaccg ctgacgtctg tccctggcct   7920
caggagcagg agcgagaggg gggaaggaca cccacgctgg agatccttaa gagccacatc   7980
tcaggaatct tccgccccaa gttctcggtg agtggcgccc agcctgggcc cccctactgt   8040
tgtgtttcga gtttaatcac tgggatgtcc tagagaggag gctctgccca ggctgcttgt   8100
attgggaagt tcctctcttc cctgggattc caggctgcaa atgtccccag accctgcccc   8160
tgtgacccct ccctttccat cgccccagtg tgctaaaggg accagcaacc tcgactattc   8220
catggctctc cctgcttcag gagcggttgg gggcctgtgg cctggaggag gaggcaccag   8280 cttggttgg ggtcttcctg cctgggcttc ccttcccagc tctgcccagc gtgagcctgg   8340
gccagtccag tgcccactcc aggggcctgt ggatggctct gcatgccact ccatggttgt   8400
aagggctgag ggcatatagg ggggagagag agacccccgg ctgcccccac ggcctcttca   8460
acaaggtggt taagtgactc ctcctcgatc tcccttgcc cagctccctc caccgctgca   8520
gctcattccg gaggtgcaga agcccctgca tgagcagctg tggtaccacg gggccatccc   8580
gagggcagag gtggctgagc tgctggtgca ctctggggac ttcctggtgc gggagagcca   8640
gggcaagcag gagtacgtgc tgtcggtgct gtgggatggt ctgccccggc acttcatcat   8700
ccagtccttg gatgtgagtg gggctgggac ccgagccttc caggcctcac tcttcccctc   8760
ccttcccttc cccaagggaa atggccttc agggtagggg gtagctgcca ggtcttggat   8820
gcctccctag cagggctggc tggaaggggc cacagagacc accctgtccc tgcaacaaaa   8880
tagaggctta agtgtgagtc ctcccctggt ggggcagcag gatgtcatgt gccatcagat   8940
ggcatctttt ctggaggtct ctctgcccct ggtcctgggc aggccctttc tccctgctg   9000 ctctccctt cccctccca gggctcacgc ccctcagaa tggaggctgc tgaccccggg   9060
tcccctgccc tgcagaacct gtaccgactg gaagggaag gctttcctag cattcctttg   9120
ctcatcgacc acctactgag cacccagcag ccctcacca agaagagtgg tgttgtcctg   9180
cacagggctg tgcccaaggt gagcctgcac ccagcctggc ccatgccacc tgtggcaggg   9240
cttggggagt gtgggtcagg cccacccagc gtctgagcag aaagggcttt ccaggccctc   9300
cgtctacata caagatgcag agtgagtgac cctcagggcc agccttgctc taggtttgga   9360
atgtcagggc cactccctatg ccatgggctg tacacaccag gttggtgctt acctggtcag   9420
ggcacctgcc tggaccccgt agtcatctca gtgtgctccc cacgtggtcc caccctggt   9480
```

```
cacatatgga ggcgccaaaa aatggaggac acagcccttc taagggccca gcaccccttt    9540
tcttcagact tctgatcccc tgtctcctct cttccccagg acaagtgggt gctgaaccat    9600
gaggacctgg tgttgggtga gcagattgga cgggtgagtg cgcctctgct ggcctccttg    9660
tcgctggcga cttctcctga gtcgcgcctg gccccctgc cctaccaccc agaaacctcc     9720
ctgccccatc tgattcccca cttgtacccc gactccctgc ccagccccca ccacacacca    9780
tcctccagga aacgggacag tacctacgct gaaaactccc agcagacagc tctgccagca    9840
ccctgacctc atcacccca cccaggccgc cccatcgag ctcttgtgtg cacgcaggga      9900
gacaccctgt tactgtaagc cataagatac ctgtttaggg aagaagtcac tgtcctaaaa    9960
atcagaatgc ttttcaaacc caaggggagag tgatttttgg atttccatgt cacttctctc   10020
aggaagggtg gcacatcgga ggcaactttc cctgcctgcc ccatgtgctc tctaggttcc    10080
ccagcgaggg tcaaactccc agagagcctg gtggaggg tccgaacacg ggggcccctc      10140 acccagggt aggaagcaga atgggtagga agcggagaag agaactgcgg gactgggaag     10200
gccgtggtag gagcccaaga ccgtttcagg ggaactttgg cgaagtgttc agcggacgcc    10260
tgcgagccga caacaccctg gtggcggtga agtcttgtcg agagacgctc ccacctgacc    10320
tcaaggccaa gttctacag gaagcgaggt gggtgataaa ctaatgatca ccacgggtcc     10380
cgcatacaca gaggttacac tgcatggcac agtgtgaagt gcttgaccac cgtggtggtg    10440
tttagtcctc gaggccccc attgcgggta gtaccccctt atagtgccga agggtagagg     10500
ctgccccagg tcacacgtcc gggtctgctg gccttggagg ccaagctctt ctcccatcat    10560
ccctgggggg ccctgggag gcgggcctgg ccacgtagat cctgagcagc agtgccctcc    10620
aggatcctga agcagtacag ccaccccaac atcgtgcgtc tcattggtgt ctgcacccag    10680
aagcagccca tctacatcgt catggagctt gtgcaggtg agcgcggggc gctgagctcc     10740
aggtagggcg cgcagcctgg tcaggtggca gccttacctc aggaggctca gcaggggtcc    10800 tcccacctg caggggcga cttcctgacc ttcctccgca cggaggggc ccgcctgcgg       10860 gtgaagactc tgctgcagat ggtgggggat gcagctgctg gcatgagta cctggagagc    10920 aagtgctgca tccaccggtg agtgggcggt ggccacgggc cctgccaaca ccccgacca    10980 gagtcaagag gtacctatac ccctaggcc ccccgctgga ccatcaggca tcagctccag    11040
agggggagtt ggcctctgtg gtagacaggg gtgcccaggg ccgggagcag cttttgtcct   11100
tggctttcct agagtgttca gccagggctg ggcaggcgac tgttggccaa atgagcccct   11160
gccctgtctc acccagggac ctggctgctc ggaactgcct ggtgacagag aagaatgtcc   11220
tgaagatcag tgactttggg atgtcccgag aggaagccga tggggtctat gcagcctcag   11280 gggcctcag acaagtcccc gtgaagtgga ccgcacctga ggcccttaac tacggtacct    11340
agtccctgtc taccctggac tccatggcca gaggccaggc ctgggtcctg ccggctgcct   11400
cgccctggcc ccagggaggg tgcactcacg ctgcctcacc tcctcgcctc ctctgcaggc   11460
cgctactcct ccgaaagcga cgtgtggagc tttggcatct tgctctggga gccttcagc    11520 ctgggggcct ccccctatcc caacctcagc aatcagcaga cacgggagtt tgtggagaag   11580
ggtaagcacc ctgtgatgac agcagcctca ggctgcaccc tcttccagat gctccagccg   11640
gactcttcta actcccttaa tgccaacctt cccaccaggc agaataagaa taacctggcc   11700
agttgctcac gcctgtcatc ccagcacttt gggaggctga gctgggtgga tcacttgagc   11760
ccaggagttc aagatcagct tggacaacac agtgaaactc catctgtaca aaaaatacaa   11820
aaatagactg ggcacggtgg ctcacacctg taatcccagc actttgggag gccgaggcag   11880
```

```
gtggatcacc tgtggtcagg agtttgagac cagccagacc aacatggtga aaccccatct   11940
ctactaaaaa tacaaaaatt agccaggcat ggtggcacgt gcctgtaatc ccagctactt   12000
gggaggctga ggtgggagaa ttgcttgaac ccaggaggcg gaggctgcag tgagccgaga   12060
ttgtgccact gcactccagc ctgggcgaca agagtgaaac tccatctcaa aaaaaaccaa   12120
aaaacaaaaa atacaaaaat tagctgggtg tggtgacatg cgcctgtagt ccctgctact   12180
cgggaggctg aggtgggagg atcactggag cccgggaggt ggaggttgca gtgagctgag   12240
atcatgccac tgcaccccaa cctgggtgac agagagagag agagaccttg actcgaaaaa   12300
gaaaaaaacc tgggcgcagt ggctcacgcc tgtaatttca acattttggg aggctgagga   12360
aggtggatca cttgagtcta ggagtttgac actagcctgg ccaacatggc aaaacctgtc   12420
tctactaaaa atacaaaaaa ttagcgaggt gtagtggtgc aagcctgtaa tcccagctac   12480
ttgggaggct gaggcacaag aatcgcttga acctgggagg tggaggttgc agtgagctga   12540
gatcacacca ctgcattcca gcgtgggtga cagagcaaga ctccatctca gaaaagaaa   12600 aaaaaaaata gaatatccct gtagctacta ctgagtgagc acctggtctg tgctaggtca   12660
catgttattt catttgctca tcactacatg tgtggtaggg attaatatgt ccctttctca   12720
gatggaaaaa caggctggca gagggacac agctagcacg tggtaggatt aggatcagaa   12780
gccaggcctc tttgtccttt gggcccttgg tggagaacag tgcatccttc agaacagtgc   12840
atcttaagca gctcctatgg ctcatggtat ccccccagagt ctgccgagga ccctcaaact   12900
ccctcctcat gcctggtgtg ctgtgcctct cctcacaggg ggccgtctgc cctgcccaga   12960
gctgtgtcct gatgccgtgt tcaggctcat ggagcagtgc tgggcctatg agcctgggca   13020
gcggcccagc ttcagcacca tctaccagga gctgcagagc atccgaaagc ggcatcggtg   13080
aggctgggac ccccttctca agctggtggc ctctgcaggc ctaggtgcag ctcctcagcg   13140
gctccagctc atatgctgac agctcttcac agtcctggac tcctgccacc agcatccaca   13200
ctgccggcag gatgcagcgc cgtgtcctct ctgtgtccct gctgctgcca gggcttcctc   13260
ttccgggcag aaacaataaa accacttgtg cccactgaac actcctggca tgtgcactcc   13320
tctggaaggc aggtctcaga aggcacaagt gccggtatgg tggccttggg gaaggaggag   13380
gacaggcagt atgcatgggg cagagctgac atgatttagt agcagctgga tgtgagacat   13440
gcggaaggcg ggggagagat caggatgata tacaggctat ggccagatgg cggtgtcatc   13500
ccctgaaata ggattatagg aagaggatca gagcttcgag gaggatgttg agtttagaga   13560
tgttgcattt tattggagat aaagtgtgg gtgaagccag gtgtggtggt agacacctgt   13620
agtcccaggt acttgggagg ccaaggcatg tggattgctt gagcctagtt tgagaccagc   13680
ctgggcaaca tggcaaaact ccatctttac aaaaacaaaa aacaaaaaac aaaaaaccaa   13740
gtaaaattag ccaggcgtgg tggcacacac ctatagtccc agctactcag aaggctgagg   13800
taggaggatc aattgagcct cggaggtcga ggctgcagtg agctgtgatc acaccactgc   13860
attccagcct gggcaacaaa gcgaggccct gtctcaaaaa taagtaaata aaataataa   13920 ataattaatt taaatgtag atgaataggt ctggaagccc agatggagat gaaggctggc   13980
aatagatgtg tgaatcattg gcttatgaat attagagagt agctgacact atggatgcgt   14040
ataacactcg cataaaattc aggaggagat gagaagagag ttccactcaa agaagactga   14100
tgtggctgat gaggaagaaa atgcttttga gggagttgtt tctcaagatg aatttattga   14160
ggaataagat ggcagactgg ggagccttca cctcctcccc taagtcccag tgaaacctaa   14220
```

-continued

```
aaagtcatct gaaatattaa catcaccaaa agcgaagttt gagaagataa ggaagtatga   14280
acataactaa aaaacaaagt gggaaacatt tgtaatacag aacagggcaa tgaaaacctt   14340
gaagtaaaat ggccatccct caagaaagtt caggaaatag ttaacatcag ctgggtgcag   14400
tggctcacac ctataatccc agcactttgg aaggctgagg caggtggatc acctgaggtc   14460
aggagctcga gaccagtctg gccaacatag tgaaactccg tctctgctaa aaatacaaaa   14520
aaaattagcc aggcgtggtg gtgtgcacct gtaatcccag ctactctgga ggctgagaag   14580
ggagaattcc ttgaaccggg gagatgaagg ttggagtgag cagagaccgc gccattgcac   14640
tccagcctgg gcaacaagag cgaagaacaa aactatgtct caaaaaaaca aaacacagca   14700
aacaaaaatc tattttgaaa gagatgagag tgagccatat aacttgttta aacaaaagga   14760
agttgtgttg tcgtgtaatt aaatgaaaat actaggaagt gaaataatac ctccaatgga   14820
aatggtagaa agcagaactg aaaaacttct gctaggtagg atatggtagg tctctgcacg   14880
ccaccactcc cattgcaacc gctagggaaa aaacagctaa gatgaaaatg tcttttttt    14940 tcttttttt ttttttttga gatggagtct cgcgctgttg cacaggctgg agtgcagtgg   15000
cgcgatctca gttcactgca acctctgcct ctcgggttca gcgattctc  ctgcctcagc   15060 ctcctgagta gctgggatta caggcacgca tcactcacga gcggctaatt tttgtaattt   15120
tagtagagac ggggtttcaa catgttggtc aggctggtct caaactcctg acctcaaagt   15180
gacccgccca cctcggcctc ccaaagtgtt gggattacag ggatgagcca ccacgcctgg   15240
ccgaaatgtc ttatttttaa aaagaatgaa gagtggtcac agaaataaag actgaat     15297
```

<210> SEQ ID NO 4
<211> LENGTH: 822
<212> TYPE: PRT
<213> ORGANISM: Human

<400> SEQUENCE: 4

```
Met Gly Phe Ser Ser Glu Leu Cys Ser Pro Gln Gly His Gly Val Leu
 1               5                  10                  15

Gln Gln Met Gln Glu Ala Glu Leu Arg Leu Leu Glu Gly Met Arg Lys
            20                  25                  30

Trp Met Ala Gln Arg Val Lys Ser Asp Arg Glu Tyr Ala Gly Leu Leu
        35                  40                  45

His His Met Ser Leu Gln Asp Ser Gly Gly Gln Ser Arg Ala Ile Ser
    50                  55                  60

Pro Asp Ser Pro Ile Ser Gln Ser Trp Ala Glu Ile Thr Ser Gln Thr
65                  70                  75                  80

Glu Gly Leu Ser Arg Leu Leu Arg Gln His Ala Glu Asp Leu Asn Ser
                85                  90                  95

Gly Pro Leu Ser Lys Leu Ser Leu Ile Arg Glu Arg Gln Gln Leu
            100                 105                 110

Arg Lys Thr Tyr Ser Glu Gln Trp Gln Gln Leu Gln Gln Glu Leu Thr
        115                 120                 125

Lys Thr His Ser Gln Asp Ile Glu Lys Leu Lys Ser Gln Tyr Arg Ala
    130                 135                 140

Leu Ala Arg Asp Ser Ala Gln Ala Lys Arg Lys Tyr Gln Glu Ala Ser
145                 150                 155                 160

Lys Asp Lys Asp Arg Asp Lys Ala Lys Asp Lys Tyr Val Arg Ser Leu
                165                 170                 175

Trp Lys Leu Phe Ala His His Asn Arg Tyr Val Leu Gly Val Arg Ala
            180                 185                 190
```

```
Ala Gln Leu His His Gln His His Gln Leu Leu Pro Gly Leu
        195                 200                 205
Leu Arg Ser Leu Gln Asp Leu His Glu Glu Met Ala Cys Ile Leu Lys
        210                 215                 220
Glu Ile Leu Gln Glu Tyr Leu Glu Ile Ser Ser Leu Val Gln Asp Glu
225                     230                 235                 240
Val Val Ala Ile His Arg Glu Met Ala Ala Ala Ala Arg Ile Gln
            245                 250                 255
Pro Glu Ala Glu Tyr Gln Gly Phe Leu Arg Gln Tyr Gly Ser Ala Pro
            260                 265                 270
Asp Val Pro Pro Cys Val Thr Phe Asp Glu Ser Leu Leu Glu Glu Gly
        275                 280                 285
Glu Pro Leu Glu Pro Gly Glu Leu Gln Leu Asn Glu Leu Thr Val Glu
        290                 295                 300
Ser Val Gln His Thr Leu Thr Ser Val Thr Asp Glu Leu Ala Val Ala
305                 310                 315                 320
Thr Glu Met Val Phe Arg Arg Gln Glu Met Val Thr Gln Leu Gln Gln
                325                 330                 335
Glu Leu Arg Asn Glu Glu Glu Asn Thr His Pro Arg Glu Arg Val Gln
            340                 345                 350
Leu Leu Gly Lys Arg Gln Val Leu Gln Glu Ala Leu Gln Gly Leu Gln
            355                 360                 365
Val Ala Leu Cys Ser Gln Ala Lys Leu Gln Ala Gln Gln Glu Leu Leu
370                 375                 380
Gln Thr Lys Leu Glu His Leu Gly Pro Gly Glu Pro Pro Val Leu
385                 390                 395                 400
Leu Leu Gln Asp Asp Arg His Ser Thr Ser Ser Ser Glu Gln Glu Arg
                405                 410                 415
Glu Gly Gly Arg Thr Pro Thr Leu Glu Ile Leu Lys Ser His Ile Ser
            420                 425                 430
Gly Ile Phe Arg Pro Lys Phe Ser Leu Pro Pro Leu Gln Leu Ile
            435                 440                 445
Pro Glu Val Gln Lys Pro Leu His Glu Gln Leu Trp Tyr His Gly Ala
        450                 455                 460
Ile Pro Arg Ala Glu Val Ala Glu Leu Leu Val His Ser Gly Asp Phe
465                 470                 475                 480
Leu Val Arg Glu Ser Gln Gly Lys Gln Glu Tyr Val Leu Ser Val Leu
                485                 490                 495
Trp Asp Gly Leu Pro Arg His Phe Ile Ile Gln Ser Leu Asp Asn Leu
            500                 505                 510
Tyr Arg Leu Glu Gly Glu Gly Phe Pro Ser Ile Pro Leu Leu Ile Asp
        515                 520                 525
His Leu Leu Ser Thr Gln Gln Pro Leu Thr Lys Lys Ser Gly Val Val
        530                 535                 540
Leu His Arg Ala Val Pro Lys Asp Lys Trp Val Leu Asn His Glu Asp
545                 550                 555                 560
Leu Val Leu Gly Glu Gln Ile Gly Arg Gly Asn Phe Gly Glu Val Phe
                565                 570                 575
Ser Gly Arg Leu Arg Ala Asp Asn Thr Leu Val Ala Val Lys Ser Cys
            580                 585                 590
Arg Glu Thr Leu Pro Pro Asp Leu Lys Ala Lys Phe Leu Gln Glu Ala
        595                 600                 605
```

-continued

```
Arg Ile Leu Lys Gln Tyr Ser His Pro Asn Ile Val Arg Leu Ile Gly
        610             615             620
Val Cys Thr Gln Lys Gln Pro Ile Tyr Ile Val Met Glu Leu Val Gln
625             630             635             640
Gly Gly Asp Phe Leu Thr Phe Leu Arg Thr Glu Gly Ala Arg Leu Arg
                645             650             655
Val Lys Thr Leu Leu Gln Met Val Gly Asp Ala Ala Ala Gly Met Glu
            660             665             670
Tyr Leu Glu Ser Lys Cys Cys Ile His Arg Asp Leu Ala Ala Arg Asn
        675             680             685
Cys Leu Val Thr Glu Lys Asn Val Leu Lys Ile Ser Asp Phe Gly Met
    690             695             700
Ser Arg Glu Glu Ala Asp Gly Val Tyr Ala Ala Ser Gly Gly Leu Arg
705             710             715             720
Gln Val Pro Val Lys Trp Thr Ala Pro Glu Ala Leu Asn Tyr Gly Arg
                725             730             735
Tyr Ser Ser Glu Ser Asp Val Trp Ser Phe Gly Ile Leu Leu Trp Glu
            740             745             750
Thr Phe Ser Leu Gly Ala Ser Pro Tyr Pro Asn Leu Ser Asn Gln Gln
        755             760             765
Thr Arg Glu Phe Val Glu Lys Gly Gly Arg Leu Pro Cys Pro Glu Leu
    770             775             780
Cys Pro Asp Ala Val Phe Arg Leu Met Glu Gln Cys Trp Ala Tyr Glu
785             790             795             800
Pro Gly Gln Arg Pro Ser Phe Ser Thr Ile Tyr Gln Glu Leu Gln Ser
                805             810             815
Ile Arg Lys Arg His Arg
            820
```